US009066900B2

(12) United States Patent
Portnoy et al.

(10) Patent No.: US 9,066,900 B2
(45) **Date of Patent: *Jun. 30, 2015**

(54) **INTERFERON-β PRODUCTION MODULATING *LISTERIA* STRAINS AND METHODS FOR USING SAME**

(71) Applicant: The Regents of the University of California, Oakland, CA (US)

(72) Inventors: Daniel A. Portnoy, Albany, CA (US); Anat A. Herskovits, Morgan Hill, CA (US); Gregory Crimmins, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/103,548

(22) Filed: Dec. 11, 2013

(65) Prior Publication Data

US 2014/0186392 A1 Jul. 3, 2014

Related U.S. Application Data

(63) Continuation of application No. 13/601,814, filed on Aug. 31, 2012, now Pat. No. 8,679,476, which is a continuation of application No. 12/514,787, filed as application No. PCT/US2007/024359 on Nov. 21, 2007, now Pat. No. 8,277,797.

(60) Provisional application No. 60/963,230, filed on Aug. 3, 2007, provisional application No. 60/923,375, filed on Apr. 12, 2007, provisional application No. 60/860,982, filed on Nov. 22, 2006.

(51) Int. Cl.

| | |
|---|---|
| ***A61K 39/02*** | (2006.01) |
| *A61K 39/00* | (2006.01) |

(52) U.S. Cl.

CPC ............ *A61K 39/0208* (2013.01); *A61K 39/00* (2013.01); *A61K 39/02* (2013.01); *A61K 2039/522* (2013.01)

(58) Field of Classification Search

None

See application file for complete search history.

(56) References Cited

U.S. PATENT DOCUMENTS

| | | | |
|---|---|---|---|
| 4,352,523 | A | 10/1982 | Holobaugh, Jr. |
| 4,816,253 | A | 3/1989 | Likhite |
| 5,389,513 | A | 2/1995 | Baquero et al. |
| 5,643,599 | A | 7/1997 | Lee et al. |
| 5,830,702 | A | 11/1998 | Portnoy et al. |
| 6,004,815 | A | 12/1999 | Portnoy et al. |
| 6,051,237 | A | 4/2000 | Paterson |
| 6,099,848 | A | 8/2000 | Frankel et al. |
| 6,287,556 | B1 | 9/2001 | Portnoy et al. |
| 6,504,020 | B1 | 1/2003 | Frankel et al. |
| 6,599,502 | B2 | 7/2003 | Portnoy et al. |
| 6,767,542 | B2 | 7/2004 | Paterson et al. |
| 6,825,028 | B1 | 11/2004 | Von Eichel-Streiber et al. |
| 2002/0025323 | A1 | 2/2002 | Paterson et al. |
| 2004/0013690 | A1 | 1/2004 | Portnoy et al. |
| 2004/0228877 | A1 | 11/2004 | Dubensky, Jr. et al. |
| 2005/0249748 | A1 | 11/2005 | Dubensky, Jr. et al. |
| 2006/0078901 | A1 | 4/2006 | Buchreiser et al. |
| 2006/0093582 | A1 | 5/2006 | Paterson et al. |
| 2006/0104991 | A1 | 5/2006 | Paterson et al. |
| 2006/0210540 | A1 | 9/2006 | Paterson et al. |
| 2006/0233835 | A1 | 10/2006 | Paterson et al. |
| 2007/0059322 | A1 | 3/2007 | Portnoy et al. |
| 2007/0253976 | A1 | 11/2007 | Paterson et al. |
| 2007/0264279 | A1 | 11/2007 | Gravekamp et al. |

FOREIGN PATENT DOCUMENTS

| | | | |
|---|---|---|---|
| WO | 99/07861 | A1 | 2/1999 |
| WO | 99/25376 | A1 | 5/1999 |
| WO | 00/09733 | A1 | 2/2000 |
| WO | 01/77335 | A2 | 10/2001 |
| WO | 02/08431 | A1 | 1/2002 |

OTHER PUBLICATIONS

Zeevi; et al., "Listeria monocytogenes Multidrug Resistance Transporters and Cyclic Di-AMP, Which Contribute to Type I Interferon Induction, Play a Role in Cell Wall Stress", J Bacteriol (Dec. 2013), 195(23):5250-5261.

Archer; et al., "Sting-Dependent Type I IFN Production Inhibits Cell—Mediated Immunity to *Listeria monocytogenes*", PLoS Pathog (Jan. 2014), 10(1):e1003861.

Autret; et al., "Identification of New Genes Involved in the Virulence of *Listeria Monocytogenes* by Signature-Tagged Transposon Mutagenesis", Infection and Immunity (Apr. 2001), 69(4):2054-2065.

Boslego; et al., "Gonorrhea Vaccines", Vaccines and Immunotherapy, (1991), Chapter 17, pp. 211-223, Pergamon Press.

Bockmann; et al., "PrfA Mediates Specific Binding of RNA Polymerase of *Listeria Monocytogenes* to PfrA-Dependent Virulence Gene Promoters Resulting in a Transcriptionally Active Complex", Molecular Microbiology (Apr. 2000), 36(2):487-497.

Camilli; et al., "Intracellular Methicllin Selection of *Listeria Monocytogenes* Mutants Unable to Replicate in a Macrophage Cell Line", Proc. Natl. Acad. Sci. USA (Jul. 1989), 86:5522-5526.

Cossart; et al., "Listeriolysin O Is Essential for Virulence of *Listeria Monocytogenes*: Direct Evidence Obtained by Gene Complementation", Infection and Immunity (Nov. 1989), 57(11):3629-3636.

(Continued)

*Primary Examiner* — Brian J. Gangle

(74) *Attorney, Agent, or Firm* — Brett E. Field; Bozicevic, Field & Francis LLP

(57) ABSTRACT

Mutant *Listeria* bacteria that modulate interferon-B production are provided. The subject bacteria are characterized by having a mutation in a gene chosen from a TetR gene, a LadR gene, a VirR gene, a MarR gene a MdrL gene, a MdrT gene and a MdrM gene. The subject bacteria find use in a variety of applications, where representative applications of interest include, but are not limited to: (a) use of the subject bacteria as adjuvants; (b) use of the subject bacteria as delivery vectors for introducing macromolecules into a cell; (c) use of the subject bacteria as vaccines for eliciting or boosting a cellular immune response; etc.

22 Claims, 20 Drawing Sheets

(56) References Cited

OTHER PUBLICATIONS

Darji; et al., "Hyperexpression of Listeriolysin in the Nonpathogenic Species *Listeria* Innocua and High Yield Purification", Journal of Biotechnology (Aug. 1995), 43:205-212.
Dazzi; et al., "Failure of B Cells of Chronic Lymphocytic Leukemia in Presenting Soluble and Alloantigens", Clinical Immunology and Immunopathology (Apr. 1995), 75(1):26-32.
Decatur; et al., "A Pest-Like Sequence in Listeriolysin 0 Essential for *Listeria Monocytogenes* Pathogenicty", Science (Nov. 2000), 290(5493):992-995.
Dramsi; et al., "Listeriolysin O: A genuine Cytolysin Optimized for an Intracellular Parasite", Journal of Cell Biol (Mar. 2002),156(6):943-946.
Ellis; et al., "Chapter 29, New Technologies for Making Vaccines", New Vaccine Technologies WB Saunders Co., (1998), pp. 568-575.
EMBL Accession No. EU262934, Nov. 19, 2007, "*Listeria Monocytogenes* Lipoate Protein Ligase Gene, Genomic DNA Sequence" (2007).
Fortineau; et al., "Optimization of Green Fluorescent Protein Expression Vectors for in Vitro and in Vivo Detection of *Listeria Monocytogenes*", Res. MicroBiol (Jun. 2000), 151(5):353-360.
Gardan; et al., "Identification of *Listeria Monocytogenes* Genes Involved in Salt and Alkaline-PH Tolerance", Applied and Environmental Microbiology (Jun. 2003), 69(6):3137-3143.
Glomski; et al., "The *Listeria Monocytogenes* Hemolysin Has an Acidic PH Optimum to Compartmentalize Activity and Prevent Damage to Infected Host Cells", The Journal of Cell Biology (Mar. 2002), 156(6):1029-1038.
Hodgson; et al., "Generalized Transduction of Serotype 1/2 and Serotype 4B Strains of *Listeria Monocytogenes*", Molecular Microbiology (Jan. 2000), 35(2):312-313.
Huillet; et al., "LadR, A New PadR-Related Transcriptional Regulator from *Listeria Monocytogenes*, Negatively Regulates the Expression of the Multidrug Efflux Pump MdrL", FEMS Microbiology Ltr, (Jan. 2006), 254(1):87-94.
Jacobson; et al., "Adverse Events and Vaccination—The Lack of Power and Predictability of Infrequent Events in Pre-Licensure Study", Vaccine (Mar. 2001), 19(17-19):2428-2433.
Lauer; et al., "Construction, Characterization, and Use of Two *Listeria Monocytogenes* Site-Specific Phage Intergration Vectors", Journal of Bacteriology (Aug. 2002), 184(15):4177-4186.
Lee; et al., "Construction of Single-Copy Intergration Vectors for *Staphylococcus Aureus*", Gene (Jul. 1991), 103:101-105 (Abstract).
Lecce; et al., "The Calf Reo-Like Virus (Rotavirus) Vaccine: An Ineffective Immunization Agent for Rotaviral Diarrhea of Piglets", Can. J. Comp. Med (Jan. 1979), 43(1):90-93.
Leimeister-Wachter; et al., "Identification of a Gene That Positively Regulates Expression of Listeriolysin, The Major Virulence Factor of *Listeria Monocytongenes*", Proc Natl Acad Sci USA (Nov. 1990), 87(21):8336-83340.
Lety; et al., "Identification of a PEST-Like Motif in Listeriolysin O Required for Phagosomal Escape and for Virulence in *Listeria Monocytogenes*", Molecular Microbiology (Mar. 2001), 39(5):1124-1139.
Lillehaug; et al., "A highly Efficient and Stable System for Site-Speciifc Intergration of Genes and Plasmids into the Phage LC3 Attachment Site (attB) of the *Lactococcus Lactis* Chromosome", Gene (Mar. 1997), 188(1):129-136.
Loessner; et al., "Complete Nucleotide Sequence, Molecular Analysis and Genome Structure of Bacteriophage A118 of *Listeria Monocytogenes*: Implications for Phage Evolution", Molecular Microbiology (Jan. 2000), 35 (2):345-340.
Luong; et al., "Improved Single-Copy Integration Vectors for *Staphylococcus Aureus*", Journal of Microbiological Methods (Jul. 2007), 70(1):186-190.
Mandin; et al., "VirR, a response regulator critical for *Listeria monocytogenes* virulence", Mol Microbiol (Sep. 2005), 57(5):1367-1380.
McShan; et al., "Vectors Containing Streptococcal Bacteriophage Integrases for Site-Specific Gene Insertion", Methods in Cell Science (1998), 20:51-57.
Moreau; et al., "Site-specific Integration of Corynephage 16:Construction of an Integration Vector", Microbiology (Mar. 1999), 145(Pt 3):539-548.
O'Riordan; et al., "*Listeria* Intracelluar Growth and Virulence Require Host Derived Lipoic Acid", Science 302 (Oct. 2003), 302(5644):462-464.
Portnoy; et al., "The cell biology of *Listeria Monocytogenes* Infection: The Intersection of Bacterial Pathogenesis and Cell Mediated Immunity", The Journal of Cell Biology (Aug. 2002), 158(3):409-414.
Ripio; et al., "Transcriptional Activation of Virulence Genes in Wild-Type Strains of *Listeria Monocytogenes* in Response to a Change in the Exracellular Medium Composition", Res. Microbiol (Jun. 1996), 147(5):371-384.
Reiter; et al., "Transfer RNA Genes Frequently Serve as integration Sites for Prokaryoticx Genetic Elements", Nucleic Acids Res (Mar. 1989), 17(5):1907-1914.
Ripio; et al., "A Gly145Ser Substitution in the Transcriptional Activator PrfA Causes Constitutive Overexpression of Virulence Factors in *Listeria Monocytogenes*", J Bacteriol (Mar. 1997), 179(5):1533-1540.
Rossignol; et al., "Phage HK022-based Intergrative Vectors for the Insertion of Genes in the Chromosome of Multiply Marked *Escherichia Coli* Strains", FEMS Microbiology Ltrs (Jul. 2002), 213(1):45-49.
Scott; et al., "Conjugative Transposition", Annu Rev Microbiol (1995), 49:367-397.
Shaferkodt; et al., "Vector Plasmid for Insertional Mutagenesis and Directional Cloning in *Listeria* spp", Biotechniques (Nov. 1995), 19(5):720-722, 724-725.
Shen; et al., "Recombinant *Listeria Monocytogenes* as a Live Vaccine Vehicle for the Induction of Protective Anti-Vitral Cell-Mediated Immunity", Proc. Natl. Acad. Sci USA (Apr. 1995), 92:3987-3991.
Smith; et al., "Genetic Methods for Diverse Prokaryotes", Academic Press Inc., (1999), vol. 29:117-118.
Ward; et al., "Intraspecific Phylogeny and Lineage Group Identification Based on the PRFA Virulence Gene Cluster of *Listeria Monocytogenes*", J Bacteriol (Aug. 2004), 186(15):4994-5002.
Witte; et al., "Cyclic di-AMP Is Critical for *Listeria monocytogenes* Growth, Cell Wall Homeostasis, and Establishment of Infection", MBio (May-Jun. 2013), 4(3):e00282-13.
Woodward; et al., "c-di-AMP Secreted by Intracellular *Listeria monocytogenes* Activates a Host Type I Interferon Response", Science (Jun. 2010), 328(5986):1703-1705.
Yang; et al., "Construction of an Integration-Proficient Vector Based on the Site-Specific Recombination Mechanism of Enterococcal Temperate Phage", Journal of Bacteriology (Apr. 2002), 184(7):1859-1864.
Swiss; Prot Accession No. Q71YF2, Hemoloysin III of *Listeria Monocytogenes*, Retrieved online Jul. 12, 2006, http://www.expasy.org/uniprot/Q71YF2, 3 pages.
Swiss; Prot Accession No. Q4EEB1, Listeriolysin O., Retrieved online Jul. 12, 2006, http://www.expasy.org/uniprot/Q4EEB1, 3 pages.
Swiss; Prot Accession No. Q4EH75, Gene Name HLY-LLL, Protein Name Hemoloysin LLL of *Listeria Monocytogenes*, Retrieved online Jul. 12, 2006, http://www.expasy.org/uniprot/Q4EH75, 3 pages.
Swiss; Prot Accession No. Q6R6C1, Gene Name HLY, Retrieved online Jul. 12, 2006, http://www.expasy.org/uniprot/Q6R6C1, 3 pages.
Swiss; Prot Accession No. Q6R6DO, Gene Name HLY, Retrieved online Jul. 12, 2006, http://www.expasy.org/uniprot/Q6R6DO, 3 pages.
Swiss; Prot Accession No. Q724L1, Listeriolysin O., Retrieved online Jul. 12, 2006, http://www.expasy.org/uniprot/Q724L1, 4 pages.
Swiss; Prot Acession No. P13128, Listeriolysin O., Retrieved online Jul. 12, 2006, http://www.expasy.org/uniprot/P13128, 5 pages.

In a 52-hour Time Course, *tetR* and *pump1617* in Liver and Spleen Colonization

| Strain | Estimated Dose | Measured Dose |
|---|---|---|
| WT | $1.0x10^4$ | $1.20x10^4$ |
| *ladR* | $1.0x10^4$ | $6.10x10^3$ |
| *tetR* | $1.0x10^4$ | $6.90x10^3$ |
| *pump1617* | $1.0x10^4$ | $6.80x10^3$ |

Type I IFN Responses Follow Same Trends In Vivo as Originally Seen in Tissue Culture

| Strain | Estimated Dose | Measured Dose |
|---|---|---|
| WT | $1.0x10^4$ | $1.20x10^4$ |
| *ladR* | $1.0x10^4$ | $6.10x10^3$ |
| *tetR* | $1.0x10^4$ | $6.90x10^3$ |
| *pump1617* | $1.0x10^4$ | $6.80x10^3$ |

In vivo Serum L929 Analysis

FIGURE 15
IV Dose
Harvest Livers
Day: 0

NK Activation
AS07-033

- Harvest hepatocytes from mice 2 days post infection
- Create single cell suspension
- Stain and flow cytometry

| Strain | Estimated Dose | Measured Dose |
|---|---|---|
| WT | $1.0x10^3$ | $1.07x10^3$ |
| *ladR* | $1.0x10^3$ | $1.16x10^3$ |
| *tetR* | $1.0x10^3$ | $1.09x10^3$ |
| *pump 1617* | $1.0x10^3$ | $1.07x10^3$ |

All Strains Resulted in Similar Liver NK Cell Maturation Profiles

*pump1617* is Deficient in NK Cell Activation

- Gated on CD11b+/DX5+ cell populations
- Gated out CD19+ cells to remove B-cell population
- Gated out T-cell Receptor (TCR) positive cells to remove T-cells and NKT cells

*pump1617* is Has a More *Lm* Epitope-Specific CD8 Response Than WT

| Strain | Estimated Dose | Measured Dose |
|---|---|---|
| WT | $1.0x10^3$ | $9.60x10^2$ |
| *ladR* | $1.0x10^3$ | $1.00x10^3$ |
| *tetR* | $1.0x10^3$ | $1.09x10^3$ |
| *pump1617* | $1.0x10^3$ | $9.10x10^2$ |

*tetR* Has a Lower CD8 Cell Response Than WT

| Strain | Estimated Dose | Measured Dose |
|---|---|---|
| WT | $1.0x10^3$ | $9.60x10^2$ |
| *ladR* | $1.0x10^3$ | $1.00x10^3$ |
| *tetR* | $1.0x10^3$ | $1.09x10^3$ |
| *pump1617* | $1.0x10^3$ | $9.10x10^2$ |

CD4-Specific Responses are Lower in Mice Infected With *tetR* While Those Infected With *pump1617* are Higher

| Strain | Estimated Dose | Measured Dose |
|---|---|---|
| WT | $1.0x10^3$ | $9.60x10^2$ |
| *ladR* | $1.0x10^3$ | $1.00x10^3$ |
| *tetR* | $1.0x10^3$ | $1.09x10^3$ |
| *pump1617* | $1.0x10^3$ | $9.10x10^2$ |

INTERFERON-β PRODUCTION MODULATING *LISTERIA* STRAINS AND METHODS FOR USING SAME

CROSS-REFERENCE TO RELATED APPLICATIONS

This application claims the benefit under 35 U.S.C. §119 (e) of prior U.S. provisional application Ser. No. 60/860,982 filed Nov. 22, 2006, prior U.S. provisional application Ser. No. 60/923,375 filed Apr. 12, 2007 and prior U.S. provisional application Ser. No. 60/963,230 filed Aug. 3, 2007, disclosures of which applications are herein incorporated by reference.

GOVERNMENT RIGHTS

This invention was made with a government support under federal grant no. AI063302 awarded by the National Institutes of Health. The Government has certain rights in this invention.

BACKGROUND OF THE INVENTION

Interferons (also referred to as "IFN" or "IFNs") are proteins having a variety of biological activities, some of which are antiviral, immunomodulating and antiproliferative. They are relatively small, species-specific, single chain polypeptides, produced by mammalian cells in response to exposure to a variety of inducers such as viruses, polypeptides, mitogens and the like. Interferons protect animal tissues and cells against viral attack and are an important host defense mechanism. In most cases, interferons provide better protection to tissues and cells of the kind from which they have been produced than to other types of tissues and cells, indicating that human-derived interferon could be more efficacious in treating human diseases than interferons from other species.

Interferons have potential in the treatment of a large number of human cancers since these molecules have anti-cancer activity which acts at multiple levels. First, interferon proteins can directly inhibit the proliferation of human tumor cells. The anti-proliferative activity is also synergistic with a variety of approved chemotherapeutic agents such as cisplatin, 5FU and TAXOL (paclitaxel). Secondly, the immunomodulatory activity of interferon proteins can lead to the induction of an anti-tumor immune response. This response includes activation of NK cells, stimulation of macrophage activity and induction of MHC class I surface expression leading to the induction of anti-tumor cytotoxic T lymphocyte activity. In addition, interferons also play a role in cross-presentation of antigens in the immune system.

Moreover, some studies further indicate that IFN-β protein may have anti-angiogenic activity. Angiogenesis, new blood vessel formation, is critical for the growth of solid tumors. Evidence indicates that IFN-β may inhibit angiogenesis by inhibiting the expression of pro-angiogenic factors such as bFGF and VEGF. Lastly, interferon proteins may inhibit tumor invasiveness by affecting the expression of enzymes such as collagenase and elastase which are important in tissue remodeling.

Interferons also appear to have antiviral activities that are based on two different mechanisms. For instance, type I interferon proteins (α and β) can directly inhibit the replication of human hepatitis B virus ("HBV") and hepatitis C virus ("HCV"), but can also stimulate an immune response which attacks cells infected with these viruses.

The method of administering interferon is an important factor in the clinical application of this important therapeutic agent. Systemic administration of interferon protein by either intravenous, intramuscular or subcutaneous injection has been most frequently used with some success in treating disorders such as hairy cell leukemia, Acquired Immune Deficiency Syndrome (AIDS) and related Kaposi's sarcoma. It is known, however, that proteins in their purified form are especially susceptible to degradation. In particular, for interferon-β, the primary mechanism(s) of interferon degradation in solution are aggregation and deamidation. The lack of interferon stability in solutions and other products has heretofore limited its utility. Therefore, a more effective method of modulating the level of interferons, such as interferon-β, is needed.

SUMMARY OF THE INVENTION

Mutant *Listeria* bacteria that modulate interferon-β production are provided. The subject bacteria are characterized by having a mutation which modulates the expression of a multidrug resistance transporter. The subject bacteria find use in a variety of applications, where representative applications of interest include, but are not limited to: (a) use of the subject bacteria as adjuvants; (b) use of the subject bacteria as delivery vectors for introducing macromolecules into a cell; (c) use of the subject bacteria as vaccines for eliciting or boosting a cellular immune response; etc.

The present invention provides a *Listeria* bacterium having a mutation which modulates the expression of a multidrug resistance transporter, wherein the *Listeria* bacterium modulates interferon-β production in macrophages. In some embodiments, the mutation is a mutation in a transcription regulator gene. In some embodiments, the transcription regulator gene is chosen from a TetR gene, a LadR gene, a VirR gene, and a MarR gene. In some embodiments, the mutation is a mutation in a multidrug resistance transporter gene. In some embodiments, the multidrug resistance transporter gene is chosen from a MdrL gene, a MdrT gene and a MdrM gene. In some embodiments, the mutation in the transcription regulator or multidrug resistance transporter gene is an insertion mutation. In some embodiments, the mutation in the transcription regulator or multidrug resistance transporter gene is a deletion mutation. In certain embodiments, the *Listeria* bacterium is *Listeria monocytogenes*. In further embodiments, the *Listeria* bacterium is attenuated.

In some embodiments, the *Listeria* bacterium increases interferon-β production in macrophages as compared to a wild type *Listeria* bacterium. In other embodiments, the *Listeria* bacterium decreases interferon-β production in macrophages as compared to a wild type *Listeria* bacterium.

In some embodiments, the bacterium includes a heterologous nucleic acid. In further embodiments, the heterologous nucleic acid is integrated. In some embodiments, the heterologous nucleic acid encodes at least one product. In certain embodiments, the at least one product is an antigen. In some embodiments, the bacterium further includes a mutation in a UvrA gene and/or a UvrB gene.

In some embodiments, the *Listeria* bacterium induces an altered Type I interferon response in an infected subject as compared to a wild type *Listeria* bacterium. In further embodiments, the CD4+ and/or CD8+ T cell specific response to *Listeria* epitopes is altered in the *Listeria* bacterium as compared to a wild type *Listeria* bacterium.

The present invention also provides a *Listeria* bacterium having a mutation in a gene chosen from a TetR gene, a LadR gene, a VirR gene, a MarR gene, a MdrL gene, a MdrT gene and a MdrM gene. In some embodiments, the mutation is an insertion mutation. In some embodiments, the mutation is a deletion mutation. In certain embodiments, the *Listeria* bacterium is *Listeria monocytogenes*. In further embodiments, the *Listeria* bacterium is attenuated.

In some embodiments, the bacterium includes a heterologous nucleic acid. In further embodiments, the heterologous nucleic acid is integrated. In some embodiments, the heterologous nucleic acid encodes at least one product. In certain embodiments, the at least one product is an antigen. In some embodiments, the bacterium further includes a mutation in a UvrA gene and/or a UvrB gene.

The present invention also provides a vaccine including attenuated *Listeria* bacteria having a mutation which modulates the expression of a multidrug resistance transporter, wherein the attenuated *Listeria* bacterium modulates interferon-β production in macrophages. In some embodiments, the mutation is a mutation in a transcription regulator gene. In some embodiments, the transcription regulator gene is chosen from a TetR gene, a LadR gene, a VirR gene, and a MarR gene. In some embodiments, the mutation is a mutation in a multidrug resistance transporter gene. In some embodiments, the multidrug resistance transporter gene is chosen from a MdrL gene, a MdrT gene and a MdrM gene. In some embodiments, the mutation in the transcription regulator or multidrug resistance transporter gene is an insertion mutation. In some embodiments, the mutation in the transcription regulator or multidrug resistance transporter gene is a deletion mutation. In certain embodiments, the *Listeria* bacterium is *Listeria monocytogenes*. In some embodiments, the bacterium further includes a mutation in a UvrA gene and/or a UvrB gene.

The present invention also provides a method of eliciting or boosting a cellular immune response in a subject by administering to the subject an effective amount of a vaccine including attenuated *Listeria* bacteria having a mutation which modulates the expression of a multidrug resistance transporter, wherein the attenuated *Listeria* bacterium modulates interferon-n production in macrophages.

The present invention also provides a method for modulating interferon-β production in a human subject by administering to a human subject an effective amount of an attenuated *Listeria* bacterium having a mutation which modulates the expression of a multidrug resistance transporter, wherein the *Listeria* bacterium modulates interferon-β production in macrophages, wherein the administering modulates interferon-β production in the human subject.

In some embodiments, the mutation is a mutation in a transcription regulator gene. In some embodiments, the transcription regulator gene is chosen from a TetR gene, a LadR gene, a VirR gene, and a MarR gene. In some embodiments, the mutation is a mutation in a multidrug resistance transporter gene. In some embodiments, the multidrug resistance transporter gene is chosen from a MdrL gene, a MdrT gene and a MdrM gene. In some embodiments, the mutation in the transcription regulator or multidrug resistance transporter gene is an insertion mutation. In some embodiments, the mutation in the transcription regulator or multidrug resistance transporter gene is a deletion mutation. In certain embodiments, the *Listeria* bacterium is *Listeria monocytogenes*. In some embodiments, the bacterium further includes a mutation in a UvrA gene and/or a UvrB gene. In some embodiments, the *Listeria* bacterium increases interferon-β production in macrophages as compared to a wild type *Listeria* bacterium. In other embodiments, the *Listeria* bacterium decreases interferon-β production in macrophages as compared to a wild type *Listeria* bacterium.

In some embodiments, the human subject has a neoplastic condition, such as cancer. In some embodiments, the human subject has a viral infection, such as a Hepatitis C viral infection. In some embodiments, the human subject has multiple sclerosis.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
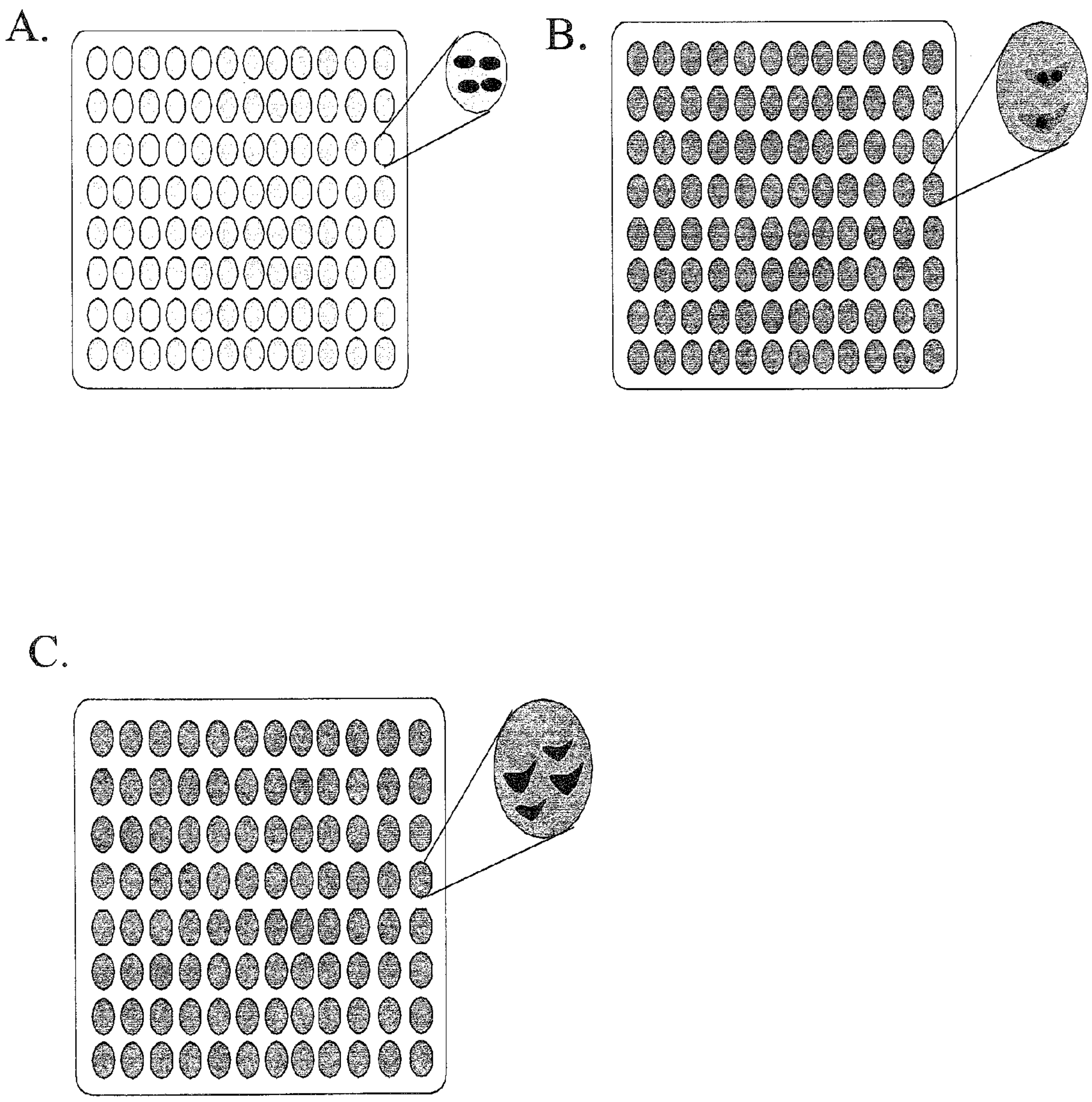
FIG. 1 is a schematic showing an exemplary screen of *Listeria monocytogenes* candidates to identify mutant bacteria that modulate IFN-β production in macrophages. Panel A shows candidate *Listeria monocytogenes* mutants grown in 96 well plates overnight in BHI media. Panel B shows the addition of *L. monocytogenes* to macrophage cultures and incubation for a period of time to allow infection of the macrophages by the candidate mutant *L. monocytogenes* (T=0, infection of the macrophages; T=1 hour, macrophages are washed and gentamicin is added; T=6 hours, supernatant is removed). Panel C shows testing of the supernatants to identify candidate stains that modulate IFN-β production. ISRE cells are plated overnight and then the supernatants from panel B are added and incubated for a period of time sufficient to reporter molecule detection. After the incubation, luciferase reagents are added and the luminescence measured from each well to determine cultures of *L. monocytogenes* that modulate IFN-β production.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All references cited in the present disclosure are herein incorporated by reference exactly as though each were individually incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Overview

Mutant *Listeria* bacteria that modulate interferon-β production are provided. The subject bacteria are characterized by having a mutation in a transcription regulator gene chosen from a TetR gene, a LadR gene, a VirR gene. and a MarR gene, or a mutation in a multidrug resistance transporter gene chosen from a MdrL gene, a MdrT gene and a MdrM gene. The subject bacteria find use in a variety of applications, where representative applications of interest include, but are not limited to: (a) use of the subject bacteria as adjuvants; (b) use of the subject bacteria as delivery vectors for introducing macromolecules into a cell; (c) use of the subject bacteria as vaccines for eliciting or boosting a cellular immune response; etc.

In further describing the subject invention, the subject mutant *Listeria* bacteria are reviewed first in greater detail, followed by a review of representative applications in which the subject vectors and methods find use.

Compositions

As noted above, the present invention provides mutant *Listeria* bacteria that include a mutation which modulates the expression of a multidrug resistance transporter, wherein the *Listeria* bacteria modulate interferon-β production, e.g., in macrophages. The term "modulates" as used here refers to an increase or a decrease in interferon-β production. In some embodiments, the modulation is an increase or decrease of at least about 10%, at least about 20%, at least about 30%, at least about 40%, at least about 50%, at least about 60%, at least about 70%, at least about 80%, at least about 90%, at least about 95%, or at least about 100% as compared to a *Listeria* bacteria that does not include the mutation.

In some embodiments, the mutant *Listeria* bacteria increase interferon-β production as compared to *Listeria* bacteria that do not include the mutation, such as a wild type *Listeria* bacterium. In such embodiments, the increase is from about 1.5-fold increase to about 50-fold increase or more, including about 2-fold increase to about 45-fold increase, about 5-fold increase to about 40-fold increase, about 10-fold increase to about 35-fold increase, about 15-fold increase to about 30-fold increase, about 20-fold increase to about 30-fold increase, and the like.

In other embodiments, the mutant *Listeria* bacteria decrease interferon-β production as compared to *Listeria* bacteria that do not include the mutation. In such embodiments, the increase is from about 1.5-fold decrease to about 50-fold decrease or more, including about 2-fold decrease to about 45-fold decrease, about 5-fold decrease to about 40-fold decrease, about 10-fold decrease to about 35-fold decrease, about 15-fold decrease to about 30-fold decrease. about 20-fold decrease to about 30-fold decrease, and the like.

In certain embodiments, mutant species according to the subject invention are ones that modulate (e.g., increase or decrease) interferon-β production as compared to their corresponding wild type strain in a macrophage cell culture as described in the Experimental section, below. In this assay, macrophages are infected with test and reference, e.g., wild-type, strains of bacteria. Following a period of time, e.g., 4 to 18 hours, the macrophage culture media is collected and the amount of Type I interferon secreted by the macrophages is detected using a reporter gene such as luciferase cloned under regulation of a Type I interferon signaling pathway. The level of the reporter gene is then measured test and reference, e.g., wild-type, strains of bacteria to identify mutant *Listeria* strains that modulate (e.g., increase or decrease) interferon-β production.

A "transcription regulator" as used herein typically refers to a protein (or polypeptide) which affects the transcription, and accordingly the expression, of a specified gene. A transcription regulator may refer to a single polypeptide transcription factor, one or more polypeptides acting sequentially or in concert, or a complex of polypeptides. In addition, a transcription regulator may affect the transcription, and according the expression, or a gene by directly increasing or decreasing transcription of a target gene, or by indirectly increasing or decreasing transcription of a first gene as part of cascade that then affects the transcription of the target gene.

A "multidrug resistance transporter" as used herein refers to a protein (or polypeptide) which participates in conferring to a cell resistance to multiple cytotoxic insults. A multidrug resistance transporter may refer to a single polypeptide, one or more polypeptides acting sequentially or in concert, or a complex of polypeptides. In addition, a multidrug resistance transporter may participate, directly or indirectly, in the catalysis of energy-dependent extrusion of molecules or compounds out of a cell or their partitioning into a specific intracellular compartment.

A "gene" as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence (e.g., a DNA sequence for mammals) that occupies a specific physical location (a "gene locus" or "genetic locus") within the genome of an organism. A gene can encode an expressed product, such as a polypeptide or a polynucleotide (e.g., tRNA). Typically, a gene includes coding sequences, such as, polypeptide encoding sequences, and non-coding sequences, such as, promoter sequences, and transcriptional regulatory sequences (e.g., enhancer sequences). In certain cases, a gene may share sequences with another gene(s) (e.g., overlapping genes).

Exemplary transcription regulator genes include, but are not limited to, TetR (lmo2589) as described in greater detail in Ramos et al., Microbiol Mol Biol Rev. 2005 June; 69(2): 326-356; LadR (lmo1408) as described in greater detail in Huillet et al., FEMS Microbiol Lett. 2006 January; 254(1): 87-94.; VirR (lmo1745) as described in greater detail in Mandin et al., Mol Microbiol. 2005 September; 57(5):1367-80.; and MarR (lmo1618) as described in greater detail in Martin et al., Proc Natl Acad Sci USA. 1995 Jun. 6; 92(12):5456-60.

Exemplary multidrug resistance transporter genes include, but are not limited, to members of the major facilitator superfamily including MdrL (lmo1409) as described in greater detail in Mata et al., FEMS Microbiol. Lett. 2000 Jun. 15; 187(2):185-8; MdrT (lmo2588) and MdrM (lmo1617), as described herein.

The subject bacteria may be any *Listeria* species that includes a mutation according to the subject invention. Thus, strains of *Listeria* other than *L. monocytogenes* may be used for the generation of mutants according to the present invention. In certain embodiments, the *Listeria* strain is *L. monocytogenes*.

Specific mutant *Listeria* bacteria of interest that include a mutated transcription regulator gene include, but are not limited to: DP-L5397, DP-L5396, DP-L5398, DP-L5418, DP-L5441 and DP-L5442, where these specific strains are described below in greater detail. DP-L5397, DP-L5396, DP-L5398, DP-L5418, DP-L5441 and DP-L5442 are deposited with the American Type Culture Collection depository (10801 University Boulevard, Manassas, Va. 20110-2209).

Specific mutant *Listeria* bacteria of interest that include a mutated multidrug resistance transporter gene include, but are not limited to: DP-L5449, DP-L5443, DP-L5448, DP-L5444 and DP-L5445, where these specific strains are described below in greater detail. DP-L5449, DP-L5443, DP-L5448, DP-L5444 and DP-L5445 are deposited with the American Type Culture Collection depository (10801 University Boulevard, Manassas, Va. 20110-2209).

Specific mutant *Listeria* bacteria of interest that include both a mutated transcription regulator gene and a mutated multidrug resistance transporter gene include, but are not limited to: DP-L5446, and DP-L5447, where these specific strains are described below in greater detail. DP-L5446, and DP-L5447 are deposited with the American Type Culture Collection depository (10801 University Boulevard, Manassas, Va. 20110-2209).

The above-mutant bacteria may be fabricated using a variety of different protocols. As such, generation of the subject mutant bacteria may be accomplished in a number of ways that are well known to those of skill in the art, including deletion mutagenesis, insertion mutagenesis, and mutagenesis which results in the generation of frameshift mutations, mutations which effect premature termination of a protein, or mutation of regulatory sequences which affect gene expression. Mutagenesis can be accomplished using recombinant DNA techniques or using traditional mutagenesis technology using mutagenic chemicals or radiation and subsequent selection of mutants. Representative protocols of different ways to generate mutant bacteria according to the present invention are provided in the Experimental Section, below.

In certain embodiments, the mutant *Listeria* bacteria are killed but metabolically active (KBMA). By the term "KBMA" or "killed but metabolically active" is meant that the bacteria are attenuated for entry into non-phagocytic cells and attenuated with respect to cell-to-cell spread resulting in bacteria that have greatly reduced toxicity and yet the immunogenicity of the bacteria is maintained. Such mutants include, but are not limited to, mutations in one or all uvr genes, i.e. uvrA, uvrB, uvrC, and uvrD genes as well as recA genes, or functionally equivalent genes, depending on the genus and species of the microbe. These mutations result in attenuation in the activity of the corresponding enzymes UvrA (an ATPase), UvrB (a helicase), UvrC (a nuclease), UvrD (a helicase II) and RecA (a recombinase). These mutants would typically be used in conjunction with a crosslinking compound, such as a psoralen. In one embodiment, there are attenuating mutations, such as deletions, in both uvrA and uvrB (uvrAB). KBMA mutations are further described in Brockstedt et al., Nature Med. 11, 853-860 (2005) and in U.S. Published Patent Application No. 2004/0228877.

In certain embodiments, the mutant *Listeria* bacteria are also attenuated. By the term "attenuation," as used herein, is meant a diminution in the ability of the bacterium to cause disease in an animal. In other words, the pathogenic characteristics of the attenuated *Listeria* strain have been lessened compared with wild-type *Listeria*, although the attenuated *Listeria* is capable of growth and maintenance in culture. Using as an example the intravenous inoculation of Balb/c mice with an attenuated *Listeria*, the lethal dose at which 50% of inoculated animals survive ($LD_{50}$) is preferably increased above the $LD_{50}$ of wild-type *Listeria* by at least about 10-fold, more preferably by at least about 100-fold, more preferably at least about 1,000 fold, even more preferably at least about 10,000 fold, and most preferably at least about 100,000-fold. An attenuated strain of *Listeria* is thus one which does not kill an animal to which it is administered, or is one which kills the animal only when the number of bacteria administered is vastly greater than the number of wild type non-attenuated bacteria which would be required to kill the same animal. An attenuated bacterium should also be construed to mean one which is incapable of replication in the general environment because the nutrient required for its growth is not present therein. Thus, the bacterium is limited to replication in a controlled environment wherein the required nutrient is provided. The attenuated strains of the present invention are therefore environmentally safe in that they are incapable of uncontrolled replication.

In certain embodiments, the attenuated mutant *Listeria* bacteria according to the subject invention are ones that exhibit a decreased virulence compared to their corresponding wild type strain in the Competitive Index Assay as described in Auerbach et al., "Development of a Competitive Index Assay To Evaluate the Virulence of *Listeria monocytogenes* actA Mutants during Primary and Secondary Infection of Mice." Infection and Immunity, September 2001, p. 5953-5957, Vol. 69, No. 9. In this assay, mice are inoculated with test and reference, e.g., wild-type, strains of bacteria. Following a period of time, e.g., 48 to 60 hours, the inoculated mice are sacrificed and one or more organs, e.g., liver, spleen, are evaluated for bacterial abundance. In these embodiments, a given bacterial strain is considered to be less virulent if its abundance in the spleen is at least about 50-fold, or more, such as 70-fold or more less than that observed with the corresponding wild-type strain, and/or its abundance in the liver is at least about 10-fold less, or more, such as 20-fold or more less than that observed with the corresponding wild-type strain.

In yet other embodiments, bacteria are considered to be less virulent if they show abortive replication in less than about 8 hours, such as less than about 6 hours, including less than about 4 hours, as determined using the assay described in Jones and Portnoy, Intracellular growth of bacteria. (1994b) *Methods Enzymol.* 236:463-467. In yet other embodiments, bacteria are considered to be attenuated or less virulent if, compared to wild-type, they form smaller plaques in the plaque assay employed in the Experimental Section, below, where cells, such as murine L2 cells, are grown to confluency, e.g., in six-well tissue culture dishes, and then infected with bacteria. Subsequently, DME-agar containing gentamicin is added and plaques are grown for a period of time, e.g., 3 days. Living cells are then visualized by adding an additional DME-agar overlay, e.g., containing neutral red (GIBCO BRL) and incubated overnight. In such an assay, the magnitude in reduction in plaque size observed with the attenuated mutant as compared to the wild-type is, in certain embodiments, 10%, including 15%, such as 25% or more.

In certain embodiments, the subject bacteria are cytotoxic. A particular strain of bacteria is considered to be cytotoxic if it compromises its host cell in a period of less than about 8 hours, sometimes less than about 6 hours, e.g., in less than about 5 hours, less than about 4 hours, less than about 3 hours, less than about two hours, or less than about 1 hour, as determined using the cytotoxicity assay described below.

In certain embodiments, mutant bacteria according to the subject invention express a heterologous antigen. The heterologous antigen is, in certain embodiments, one that is capable of providing protection in an animal against challenge by the infectious agent from which the heterologous antigen was derived, or which is capable of affecting tumor growth and metastasis in a manner which is of benefit to a host organism. Heterologous antigens which may be introduced into a *Listeria* strain of the subject invention by way of DNA encoding the same thus include any antigen which when expressed by *Listeria* serves to elicit a cellular immune response which is of benefit to the host in which the response is induced. Heterologous antigens therefore include those specified by infectious agents, wherein an immune response directed against the antigen serves to prevent or treat disease caused by the agent. Such heterologous antigens include, but are not limited to, viral, bacterial, fungal or parasite surface proteins and any other proteins, glycoproteins, lipoprotein, glycolipids, and the like. Heterologous antigens also include those which provide benefit to a host organism which is at risk for acquiring or which is diagnosed as having a tumor that expresses the said heterologous antigen(s). The host organism is preferably a mammal and most preferably, is a human.

By the term "heterologous antigen," as used herein, is meant a protein or peptide, a lipoprotein or lipopeptide, or any other macromolecule which is not normally expressed in *Listeria*, which substantially corresponds to the same antigen in an infectious agent, a tumor cell or a tumor-related protein. The heterologous antigen is expressed by a strain of *Listeria* according to the subject invention, and is processed and presented to cytotoxic T-cells upon infection of mammalian cells by the strain. The heterologous antigen expressed by *Listeria* species need not precisely match the corresponding unmodified antigen or protein in the tumor cell or infectious agent so long as it results in a T-cell response that recognizes the unmodified antigen or protein which is naturally expressed in the mammal. In other examples, the tumor cell antigen may be a mutant form of that which is naturally expressed in the mammal, and the antigen expressed by the *Listeria* species will conform to that tumor cell mutated antigen. By the term "tumor-related antigen," as used herein, is meant an antigen which affects tumor growth or metastasis in a host organism. The tumor-related antigen may be an antigen expressed by a tumor cell, or it may be an antigen which is expressed by a non-tumor cell, but which when so expressed, promotes the growth or metastasis of tumor cells. The types of tumor antigens and tumor-related antigens which may be introduced into *Listeria* by way of incorporating DNA encoding the same, include any known or heretofore unknown tumor antigen. In other examples, the "tumor-related antigen" has no effect on tumor growth or metastasis, but is used as a component of the *Listeria* vaccine because it is expressed specifically in the tissue (and tumor) from which the tumor is derived. In still other examples, the "tumor-related antigen" has no effect on tumor growth or metastasis, but is used as a component of the *Listeria* vaccine because it is selectively expressed in the tumor cell and not in any other normal tissues.

The heterologous antigen useful in vaccine development may be selected using knowledge available to the skilled artisan, and many antigenic proteins which are expressed by tumor cells or which affect tumor growth or metastasis or which are expressed by infectious agents are currently known. For example, viral antigens which may be considered as useful as heterologous antigens include but are not limited to the nucleoprotein (NP) of influenza virus and the gag protein of HIV. Other heterologous antigens include, but are not limited to, HIV env protein or its component parts gp120 and gp41, HIV nef protein, and the HIV pol proteins, reverse transcriptase and protease. Still other heterologous antigens can be those related to hepatitis C virus (HCV), including but not limited to the E1 and E2 glycoproteins, as well as non-structural (NS) proteins, for example NS3. In addition, other viral antigens such as herpesvirus proteins may be useful. The heterologous antigens need not be limited to being of viral origin. Parasitic antigens, such as, for example, malarial antigens, are included, as are fungal antigens, bacterial antigens and tumor antigens.

As noted herein, a number of proteins expressed by tumor cells are also known and are of interest as heterologous antigens which may be inserted into the vaccine strain of the invention. These include, but are not limited to, the bcr/abl antigen in leukemia, HPVE6 and E7 antigens of the oncogenic virus associated with cervical cancer, the MAGE1 and MZ2-E antigens in or associated with melanoma, and the MVC-1 and HER-2 antigens in or associated with breast cancer. Other coding sequences of interest include, but are not limited to, costimulatory molecules, immunoregulatory molecules, and the like.

The introduction of DNA encoding a heterologous antigen into a strain of *Listeria* may be accomplished, for example, by the creation of a recombinant *Listeria* in which DNA encoding the heterologous antigen is harbored on a vector, such as a plasmid for example, which plasmid is maintained and expressed in the *Listeria* species, and in whose antigen expression is under the control of prokaryotic promoter/regulatory sequences. Alternatively, DNA encoding the heterologous antigen may be stably integrated into the *Listeria* chromosome by employing, for example, transposon mutagenesis, homologous recombination, or integrase mediated site-specific integration (as described in U.S. patent application Ser. No. 10/136,860, the disclosure of which is herein incorporated by reference).

Several approaches may be employed to express the heterologous antigen in *Listeria* species as will be understood by one skilled in the art once armed with the present disclosure. In certain embodiments, genes encoding heterologous antigens are designed to either facilitate secretion of the heterologous antigen from the bacterium or to facilitate expression of the heterologous antigen on the *Listeria* cell surface.

In certain embodiments, a fusion protein which includes the desired heterologous antigen and a secreted or cell surface protein of *Listeria* is employed. *Listerial* proteins which are suitable components of such fusion proteins include, but are not limited to, ActA, listeriolysin O (LLO) and phosphatidylinositol-specific phospholipase (PI-PLC). A fusion protein may be generated by ligating the genes which encode each of the components of the desired fusion protein, such that both genes are in frame with each other. Thus, expression of the ligated genes results in a protein comprising both the heterologous antigen and the *Listerial* protein. Expression of the ligated genes may be placed under the transcriptional control of a *Listerial* promoter/regulatory sequence such that expression of the gene is effected during growth and replication of the organism. Signal sequences for cell surface expression and/or secretion of the fused protein may also be added to genes encoding heterologous antigens in order to effect cell surface expression and/or secretion of the fused protein. When the heterologous antigen is used alone (i.e., in the absence of fused *Listeria* sequences), it may be advantageous to fuse thereto signal sequences for cell surface expression and/or secretion of the heterologous antigen. The procedures for accomplishing this are well know in the art of bacteriology and molecular biology.

The DNA encoding the heterologous antigen which is expressed is, in many embodiments, preceded by a suitable promoter to facilitate such expression. The appropriate promoter/regulatory and signal sequences to be used will depend on the type of *Listerial* protein desired in the fusion protein and will be readily apparent to those skilled in the art of *Listeria* molecular biology. For example, suitable *L. monocytogenes* promoter/regulatory and/or signal sequences which may be used to direct expression of a fusion protein include, but are not limited to, sequences derived from the *Listeria* hly gene which encodes LLO, the *Listeria* p60 (iap) gene, and the *Listeria* actA gene which encodes a surface protein necessary for *L. monocytogenes* actin assembly. Other promoter sequences of interest include the plcA gene which encodes PI-PLC, the *Listeria* mpl gene, which encodes a metalloprotease, and the *Listeria* inlA gene which encodes internalin, a *Listeria* membrane protein. The heterologous regulatory elements such as promoters derived from phage and promoters or signal sequences derived from other bacterial species may be employed for the expression of a heterologous antigen by the *Listeria* species.

In certain embodiments, the mutant *Listeria* include a vector. The vector may include DNA encoding a heterologous antigen. Typically, the vector is a plasmid that is capable of replication in *Listeria*. The vector may encode a heterologous antigen, wherein expression of the antigen is under the control of eukaryotic promoter/regulatory sequences, e.g., is present in an expression cassette. Typical plasmids having suitable promoters that are of interest include, but are not limited to, pCMV-β comprising the immediate early promoter/enhancer region of human cytomegalovirus, and those which include the SV40 early promoter region or the mouse mammary tumor virus LTR promoter region.

As such, in certain embodiments, the subject bacteria include at least one coding sequence for heterologous polypeptide/protein, as described above. In many embodiments, this coding sequence is part of an expression cassette, which provides for expression of the coding sequence in the *Listeria* cell for which the vector is designed. The term "expression cassette" as used herein refers to an expression module or expression construct made up of a recombinant DNA molecule containing at least one desired coding sequence and appropriate nucleic acid sequences necessary for the expression of the operably linked coding sequence in a particular host organism, i.e., the *Listeria* cell for which the vector is designed, such as the promoter/regulatory/signal sequences identified above, where the expression cassette may include coding sequences for two or more different polypeptides, or multiple copies of the same coding sequence, as desired. The size of the coding sequence and/or expression cassette that includes the same may vary, but typically falls within the range of about 25-30 to about 6000 bp, usually from about 50 to about 2000 bp. As such, the size of the encoded product may vary greatly, and a broad spectrum of different products may be encoded by the expression cassettes present in the vectors of this embodiment.

As indicated above, the vector may include at least one coding sequence, where in certain embodiments the vectors include two or more coding sequences, where the coding sequences may encode products that act concurrently to provide a desired results. In general, the coding sequence may encode any of a number of different products and may be of a variety of different sizes, where the above discussion merely provides representative coding sequences of interest.

Adjuvant Compositions

The subject mutant bacterial strains also find use as immunopotentiating agents, i.e., as adjuvants. In such applications, the subject attenuated bacteria may be administered in conjunction with an immunogen, e.g., a tumor antigen, modified tumor cell, etc., according to methods known in the art where live bacterial strains are employed as adjuvants. See, e.g., Berd et al., Vaccine 2001 Mar. 21; 19(17-19):2565-70.

In some embodiments, the mutant bacterial strains are employed as adjuvants by chemically coupled to a sensitizing antigen. The sensitizing antigen can be any antigen of interest, where representative antigens of interest include, but are not limited to: viral agents, e.g., Herpes simplex virus; malaria parasite; bacteria, e.g., *staphylococcus aureus* bacteria, diphtheria toxoid, tetanus toxoid, shistosomula; tumor cells, e.g. $CAD_2$ mammary adenocarcinomia tumor cells, and hormones such as thyroxine $T_4$, triiiodothyronine $T_3$, and cortisol. The coupling of the sensitizing antigen to the immunopotentiating agent can be accomplished by means of various chemical agents having two reactive sites such as, for example, bisdiazobenzidine, glutaraldehyde, di-iodoacetate, and diisocyanates, e.g., m-xylenediisocyanate and toluene-2, 4-diisocyanate. Use of *Listeria* spp. as adjuvants is further described in U.S. Pat. No. 4,816,253.

Vaccines

The subject attenuated mutant bacteria also find use as vaccines. The vaccines of the present invention are administered to a vertebrate by contacting the vertebrate with a sublethal dose of an attenuated mutant *Listeria* vaccine, where contact typically includes administering the vaccine to the host. In many embodiments, the attenuated bacteria are provided in a pharmaceutically acceptable formulation. Administration can be oral, parenteral, intranasal, intramuscular, intradermal, intraperitoneal, intravascular, subcutaneous, direct vaccination of lymph nodes, administration by catheter or any one or more of a variety of well-known administration routes. In farm animals, for example, the vaccine may be administered orally by incorporation of the vaccine in feed or liquid (such as water). It may be supplied as a lyophilized powder, as a frozen formulation or as a component of a capsule, or any other convenient, pharmaceutically acceptable formulation that preserves the antigenicity of the vaccine. Any one of a number of well known pharmaceutically acceptable diluents or excipients may be employed in the vaccines of the invention. Suitable diluents include, for example, sterile, distilled water, saline, phosphate buffered solution, and the like. The amount of the diluent may vary widely, as those skilled in the art will recognize. Suitable excipients are also well known to those skilled in the art and may be selected, for example, from A. Wade and P. J. Weller, eds., *Handbook of Pharmaceutical Excipients* (1994) The Pharmaceutical Press: London. The dosage administered may be dependent upon the age, health and weight of the patient, the type of patient, and the existence of concurrent treatment, if any. The vaccines can be employed in dosage forms such as capsules, liquid solutions, suspensions, or elixirs, for oral administration, or sterile liquid for formulations such as solutions or suspensions for parenteral, intranasal intramuscular, or intravascular use. In accordance with the invention, the vaccine may be employed, in combination with a pharmaceutically acceptable diluent, as a vaccine composition, useful in immunizing a patient against infection from a selected organism or virus or with respect to a tumor, etc. Immunizing a patient means providing the patient with at least some degree of therapeutic or prophylactic immunity against selected pathogens, cancerous cells, etc.

The subject vaccines find use in methods for eliciting or boosting a cellular immune response, e.g., a helper T cell or a cytotoxic T-cell response to a selected agent, e.g., pathogenic organism, tumor, etc., in a vertebrate, where such methods include administering an effective amount of the *Listeria* vaccine. The subject vaccines find use in methods for eliciting in a vertebrate an innate immune response that augments the antigen-specific immune response. Furthermore, the vaccines of the present invention may be used for treatment post-exposure or post diagnosis. In general, the use of vaccines for post-exposure treatment would be recognized by one skilled in the art, for example, in the treatment of rabies and tetanus. The same vaccine of the present invention may be used, for example, both for immunization and to boost immunity after exposure. Alternatively, a different vaccine of the present invention may be used for post-exposure treatment, for example, such as one that is specific for antigens expressed in later stages of exposure. As such, the subject vaccines prepared with the subject vectors find use as both prophylactic and therapeutic vaccines to induce immune responses that are specific for antigens that are relevant to various disease conditions.

The patient may be any human and non-human animal susceptible to infection with the selected organism. The subject vaccines will find particular use with vertebrates such as man, and with domestic animals. Domestic animals include domestic fowl, bovine, porcine, ovine, equine, caprine, Leporidate (such as rabbits), or other animal which may be held in captivity.

In general, the subject vaccines find use in vaccination applications as described U.S. Pat. Nos. 5,830,702 and 6,051,237, as well as PCT publication no WO 99/25376.

Methods

The present invention also provides methods for modulating interferon-β production in a subject, by administering to a subject an effective amount of an attenuated *Listeria* bacterium comprising a mutation in a transcription regulator gene and/or multidrug resistance transporter gene, wherein the attenuated *Listeria* bacterium modulates interferon-β production in macrophages, and wherein the administering modulates interferon-β production in the subject.

As used herein "therapeutically effective amount" or "efficacious amount" means the amount of an organism or compound that, when administered to a mammal or other subject for treating a disease, is sufficient to effect such treatment for the disease. The "therapeutically effective amount" will vary depending on the organism or compound, the disease and its severity and the age, weight, etc., of the subject to be treated.

In some embodiments, subjects suitable for treatment with a method of the present invention include individuals having a cellular proliferative disease, such as a neoplastic disease (e.g., cancer). Cellular proliferative disease is characterized by the undesired propagation of cells, including, but not limited to, neoplastic disease conditions, e.g., cancer. Examples of cellular proliferative disease include, but not limited to, abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying, for example, rheumatoid arthritis, psoriasis, diabetic retinopathy, other ocular angiogenic diseases such as retinopathy of prematurity (retrolental fibroplastic), macular degeneration, corneal graft rejection, neurovascular glaucoma and Oster Webber syndrome, psoriasis, restenosis, fungal, parasitic and viral infections such cytomegaloviral infections. Subjects to be treated according to the methods of the invention include any individual having any of the above-mentioned disorders.

In other embodiments, subjects suitable for treatment with a method of the present invention include individuals who have been clinically diagnosed as infected with a hepatitis virus (e.g., HAV, HBV, HCV, delta, etc.), particularly HCV, are suitable for treatment with the methods of the instant invention. Individuals who are infected with HCV are identified as having HCV RNA in their blood, and/or having anti-HCV antibody in their serum. Such individuals include naïve individuals (e.g., individuals not previously treated for HCV, particularly those who have not previously received IFN-α-based or ribavirin-based therapy) and individuals who have failed prior treatment for HCV.

In other embodiments, subjects suitable for treatment with a method of the present invention include individuals having multiple sclerosis. Multiple sclerosis refers to an autoimmune neurodegenerative disease, which is marked by inflammation within the central nervous system with lymphocyte attack against myelin produced by oligodendrocytes, plaque formation and demyelization with destruction of the myelin sheath of axons in the brain and spinal cord, leading to significant neurological disability over time. Typically, at onset an otherwise healthy person presents with the acute or sub acute onset of neurological symptomatology (attack) manifested by unilateral loss of vision, vertigo, ataxia, dyscoordination, gait difficulties, sensory impairment characterized by paresthesia, dysesthesia, sensory loss, urinary disturbances until incontinence, diplopia, dysarthria or various degrees of motor weakness until paralysis. The symptoms are usually painless, remain for several days to a few weeks, and then partially or completely resolve. After a period of remission, a second attack will occur. During this period after the first attack, the patient is defined to suffer from probable MS. Probable MS patients may remain undiagnosed for years. When the second attack occurs the diagnosis of clinically definite MS (CDMS) is made (Poser criteria 1983; C. M. Poser et al. Ann. Neurol. 1983; 13, 227).

The terms "subject" and "patient" mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease. i.e., arresting or reducing the development of the disease or its symptoms, or (3) relieving the disease, i.e. causing regression of the disease or its clinical symptoms. As used herein, the term "treating" is thus used to refer to both prevention of disease, and treatment of pre-existing conditions. For example, where the mutant bacteria is administered, the prevention of cellular proliferation can be accomplished by administration of the subject compounds prior to development of overt disease, e.g. to prevent the regrowth of tumors, prevent metastatic growth, etc. Alternatively the compounds are used to treat ongoing disease, by stabilizing or improving the clinical symptoms of the patient.

Combination Therapy

For use in the subject methods, the subject mutant *Listeria* may be administered in combination with other pharmaceutically active agents, including other agents that treat the underlying condition or a symptom of the condition. In addition, the mutant *Listeria* may be used to provide an increase in the effectiveness of another chemical, such as a pharmaceutical, that is necessary to produce the desired biological effect.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

Examples of other agents for use in combination therapy of neoplastic disease include, but are not limited to, thalidomide, marimastat, COL-3, BMS-275291, squalamine, 2-ME, SU6668, NEOVASTAT (cartilage derived anti-angiogenic compound), Medi-522, EMD121974, CAI, celecoxib, interleukin-12, IM862, TNP470, AVASTIN (bevacizumab), GLEEVEC (imatinib), HERCEPTIN (Trastuzumab), and mixtures thereof. Examples of chemotherapeutic agents for use in combination therapy include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithrarnycin, prednisone, hydroxyprogesterone, testosterone, tamoxifen, dacarbazine, procarbazine, hexamethylmelarnine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, TAXOL (paclitaxel), vincristine, vinblastine, etoposide (VP-16), trimetrexate, irinotecan, topotecan, gemcitabine, teniposide, cisplatin and diethylstilbestrol (DES).

Other antiviral agents can also be delivered in the treatment methods of the invention. For example, compounds that inhibit inosine monophosphate dehydrogenase (IMPDH) may have the potential to exert direct anti viral activity, and such compounds can be administered in combination with the mutant *Listeria*, as described herein. Drugs that are effective inhibitors of hepatitis C NS3 protease may be administered in combination with the mutant *Listeria*, as described herein. Hepatitis C NS3 protease inhibitors inhibit viral replication. Other agents such as inhibitors of HCV NS3 helicase are also attractive drugs for combinational therapy, and are contemplated for use in combination therapies described herein. Ribozymes such as Heptazyme™ and phosphorothioate oligonucleotides which are complementary to HCV protein sequences and which inhibit the expression of viral core proteins are also suitable for use in combination therapies described herein.

Examples of other agents for use in combination therapy of multiple sclerosis include, but are not limited to; glatiramer; corticosteroids; muscle relaxants, such as Tizanidine (ZANAFLEX) and baclofen (LIORESAL); medications to reduce fatigue, such as amantadine (SYMMETREL) or modafinil (PROVIGIL); and other medications that may also be used for depression, pain and bladder or bowel control problems that can be associated with MS.

In the context of a combination therapy, combination therapy compounds may be administered by the same route of administration (e.g. intrapulmonary, oral, enteral, etc.) that the mutant *Listeria* are administered. In the alternative, the compounds for use in combination therapy with the mutant *Listeria* may be administered by a different route of administration.

Kits

Kits with unit doses of the subject mutant *Listeria*, e.g., in oral or injectable doses, are provided. In such kits, in addition to the containers containing the unit doses will be an informational package insert describing the use and attendant benefits of the mutant *Listeria* in treating a pathological condition of interest.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Generation of *Listeria monocytogenes* Transcription Regulator Gene Mutants and Characterization of Role in Modulating Interferon-β Expression Mutant Libraries Generation of *Listeria monocytogenes* mutant libraries using transposon Tn917-LTV3 was previously described (Camilli et al., 1990). Nine independent libraries were generated by A. Camilli, from which 8 libraries were screened in this study. These libraries are designated as Libraries 910-918 and are part of the Portnoy culture collection.

Genetic Screen

Figure 2:
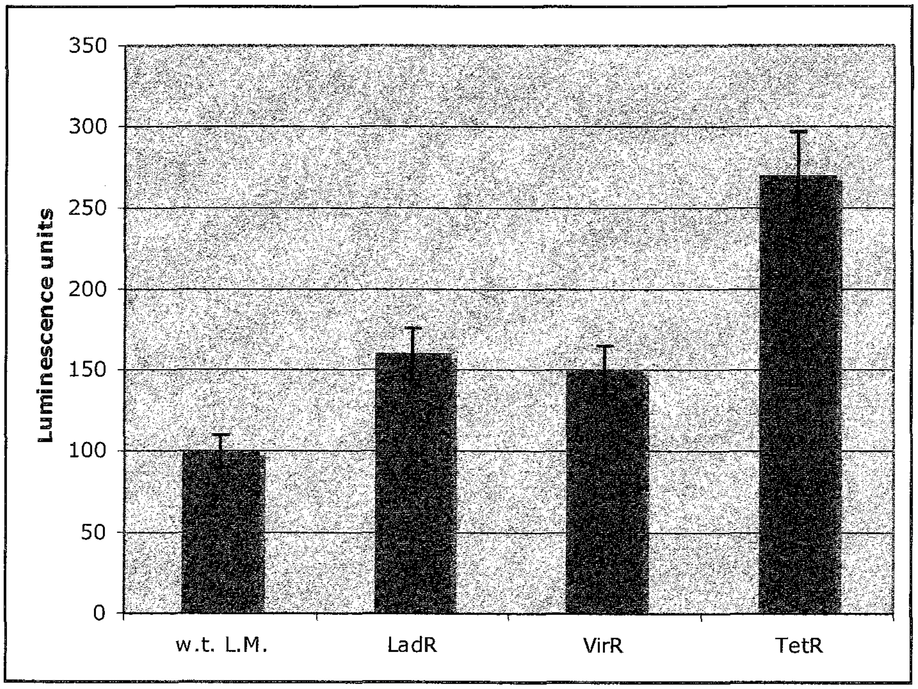
FIG. 2 is a graph showing the level of IFN-β secretion using the L-929-ISRE reporter assay for wild type *L. monocytogenes* and mutant *L. monocytogenes* strains that have a mutation in the LadR gene (DP-L5396), the VirR gene (DP-L5398), or the TetR gene (DP-L5397).

Eight independent *L. monocytogenes* Tn917-LTV3-transposon insertion libraries, were plated to single colonies on BHI agar plates and then patched (single colony per well) to 96 well plates (FIG. 1, panel A). A total of 4500 bacterial insertion mutants were grown on BHI media in 96 well plates and were frozen with glycerol for further infection experiments. Bone marrow-derived macrophages from C57Bl/6 mice femurs were prepared as described and grown for six days and frozen (Portnoy et al., 1989). Macrophages were thawed and were plated on 96 well plates, $4\times10^4$ cells/well and were infected with $1\times10^6$ of over-night grown bacterial cultures (FIG. 1, panel B). Half an hour post infection, macrophages were washed to remove extracellular bacteria and gentamicin was added at a concentration of 50 μg/ml to prevent extracellular growth of bacteria. At 6 hours post infection 100 μl of macrophages culture media was taken and frozen at −80. The amount of Type I IFN secreted by macrophages during bacterial infection was detected using the reporter gene luciferase, cloned under the regulation of Type I interferon signaling pathway in L929 cell line, ISRE-L929 (Jiang et al., 2005). ISRE-L929 cells were grown in 96 well plates and were incubated with 40 μl of infected macrophages culture media for 4 h (FIG. 1, panel C). Then, cells were lysed and luciferase activity was detected using Bright Glow Assay (Promega, E-2620) and light emission measurement by luminescence counter (VICTOR3, PerlinElmer®) (FIG. 2). Screening of mutants was done in triplicate for each mutant on the same plate and 8 replicates of wild type *L. monocytogenes* and hly-minus mutant as controls. Table 1 shows the strains characterized and used in this study, and FIG. 2 shows that the LadR, VirR, and TetR mutant *Listeria* strains had an increase in interferon-β expression over the wild type strain.

TABLE 1

| No. | Gene name | Description | Portnoy lab strain number |
|---|---|---|---|
| 1 | lmo2589 | TetR negative regulator | DP-L5397 |
| 2 | lmo1408 | LadR negative regulator | DP-L5396 |
| 3 | lmo1745 | VirR transcription regulator | DP-L5398 |
| 4 | lmo1618 | MarR transcription regulator | DP-L5442 |
| 5 | lmo2588 | Multi drug transporter regulated by TetR (lmo2589) | DP-L5416 |
| 6 | lmo1617 | Multi drug transporter regulated by MarR (lmo1618) | DP-L5417 |
| 7 | lmo1409 | Multi drug transporter regulated by LadR (mdrL) (lmo1409) | DP-L5445 |

Analysis of Mutants

Figure 3:
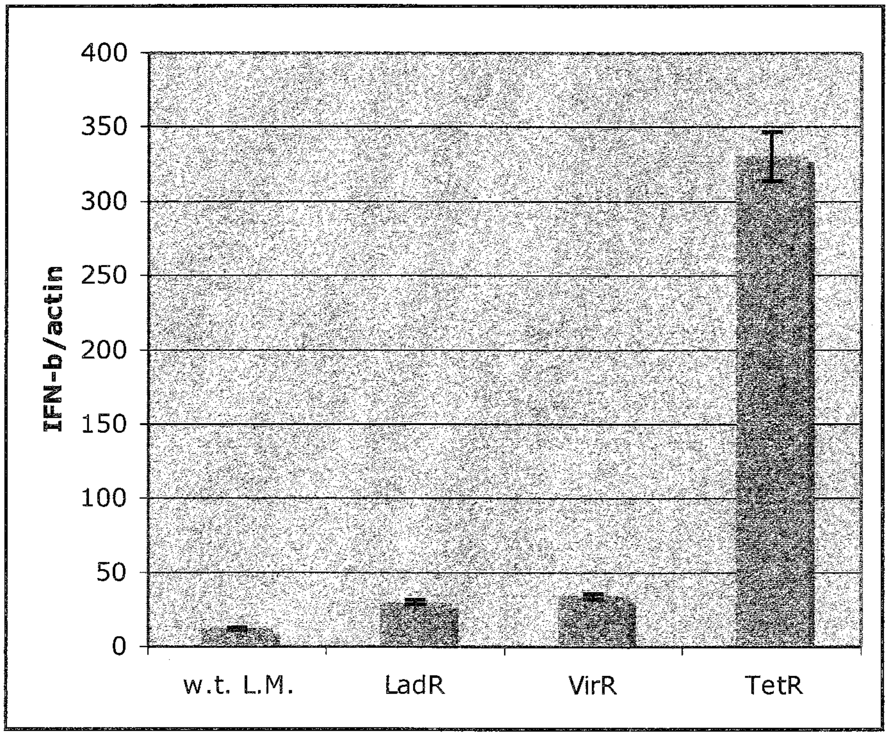
FIG. 3 is a graph showing the level of IFN-β induction as measuring by real-time Q-PCR for wild type *L. monocytogenes* and mutant *L. monocytogenes* strains that have a mutation in the LadR gene (DP-L5396), the VirR gene (DP-L5398), or the TetR gene (DP-L5397).

Analysis of IFN-β Transcription by Quantitative Real-Time PCR:

This analysis was performed as described by Auerbuch et al (Auerbuch V. et al., J Exp Med. 2004 Aug. 16; 200(4):527-33. Epub 2004 Aug. 9). For further verification of induction of IFN-β by bacterial mutants, the level of IFN-β mRNA was analyzed and compared to induction of IFN-β by wild type *L. monocytogenes*. Four hours post infection, total macrophages RNA was extracted using RNeasy kit (QIAGENE™). First strand cDNA was produced by using 1 μg of total RNA in M-MLV reverse transcriptase reaction. SYBR® Green-based quantitative PCR amplification was using SYBR® Green PCR core reagents (Applied Biosystems) and the Stratagene™ Mx3000P Real-Time PCR System. Primers used: ifnb-F: 5'-ctggagcagctgaatggaaag (SEQ ID NO:01); ifnb-R: 5'-cttgaagtccgccctgtaggt (SEQ ID NO:02); β-actin-F: 5'-aggtgtgatggtgggaatgg (SEQ ID NO:03); β-actin-R: 5'-gcctcgtcacccacatagga (SEQ ID NO:04). FIG. 3 shows that the LadR, VirR, and TetR mutant *Listeria* strains induced an increase in interferon-β mRNA expression over the wild type strain.

Figure 4:
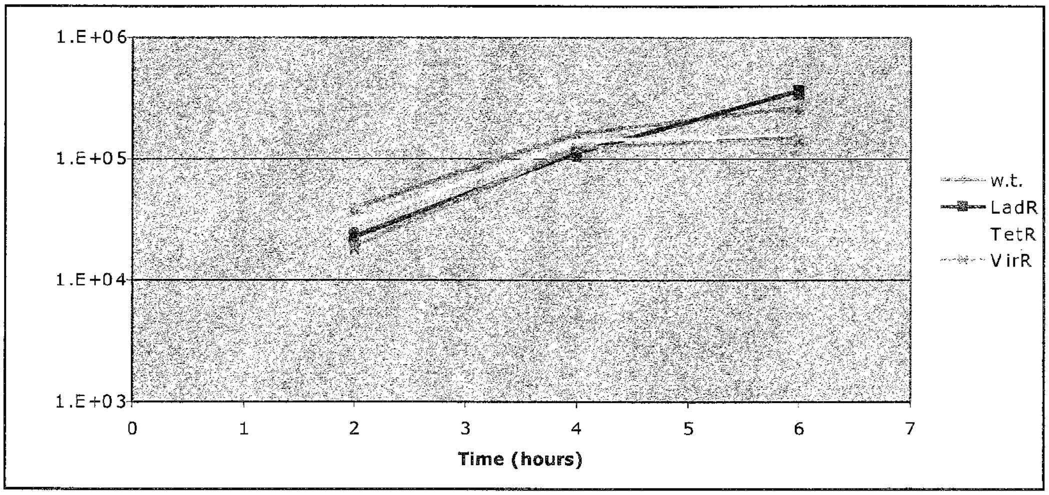
FIG. 4 is a graph showing the intracellular growth of wild type *L. monocytogenes* and mutant *L. monocytogenes* strains that have a mutation in the LadR gene (DP-L5396)(□), the VirR gene (DP-L5398)(Δ), or the TetR gene (DP-L5397)(X).

Intracellular Growth Curves:

Characterization of intracellular bacterial growth was performed using primary bone marrow derived macrophages as previously described (Portnoy et al., 1989). Briefly, approximately, $8\times10^6$ over night grown *L. monocytogenes* bacteria were used to infect $2\times10^6$ macrophages cells, which resulted in infection of 1-2 bacteria per cell. Thirty minutes after addition of bacteria macrophage monolayers were washed with PBS and media was added. At one h.p.i., gentamicin was added to 50 μg $ml^{-1}$, to limit the growth of extracellular bacteria. At 2, 4 and 6 hours post infection 3 cover slips were taken and washed with water to lyse macrophages cells. Bacteria recovered from each coverslip were plated on BHI plates and the number of bacterial colonies was counted. FIG. 4 shows that the LadR, VirR, and TetR mutant *Listeria* strains have a normal growth rate as compared to the wild type strain.

Sequencing of Tn917 Insertion Site

Figure 5:
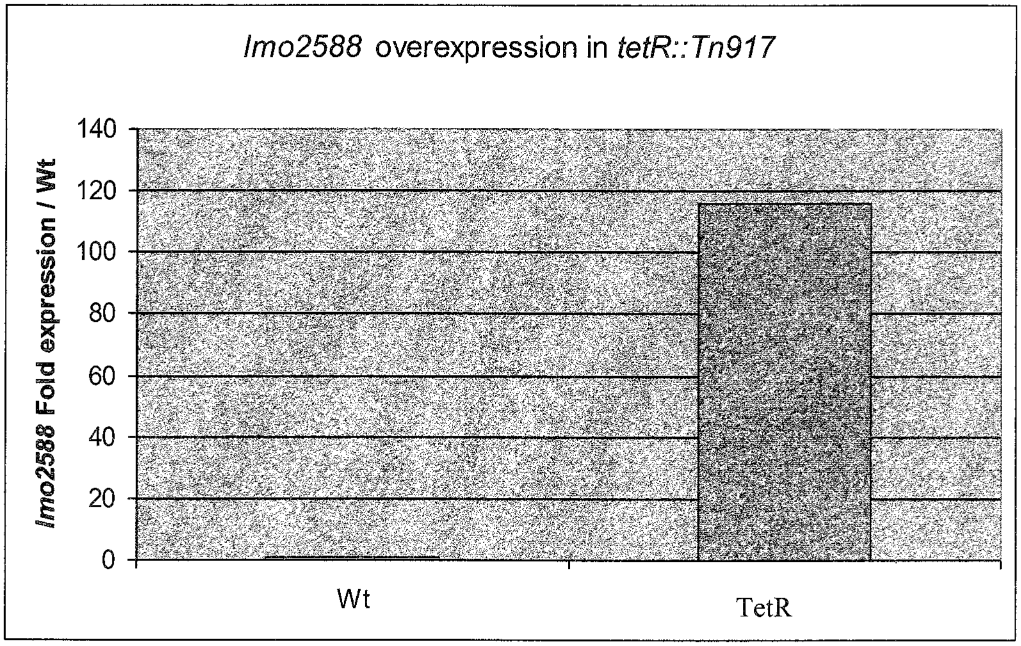
FIG. 5 is a graph showing the expression level of the lmo2588 gene (multi drug transporter regulated by TetR) in wild type *L. monocytogenes* and the TetR mutant *L. monocytogenes* strain (DP-L5397).
Figure 6:
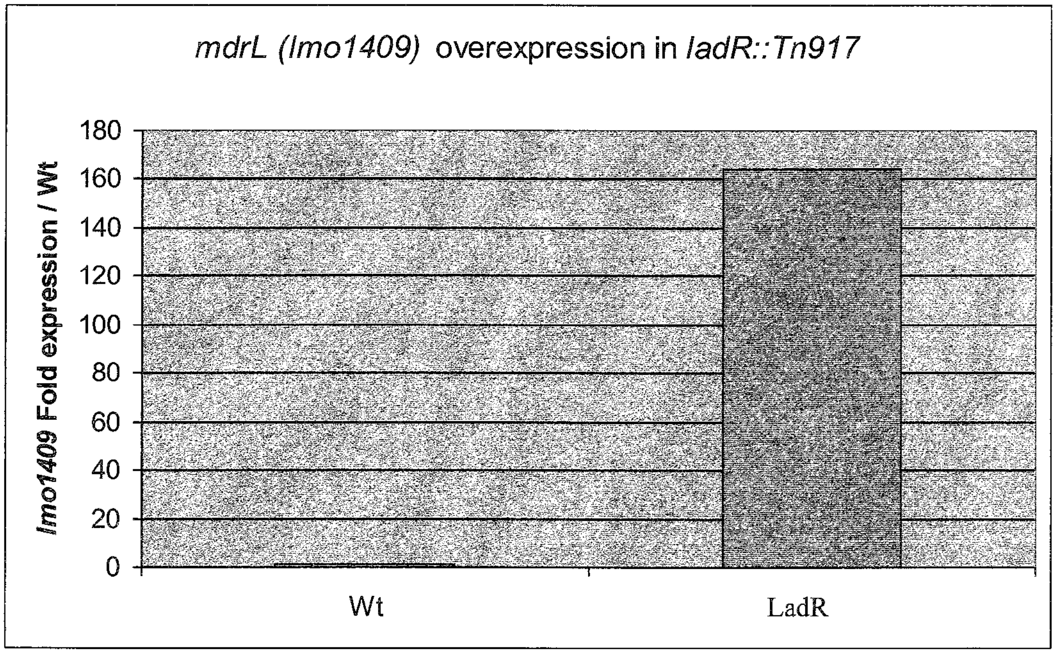
FIG. 6 is a graph showing the expression level of the lmo1409 gene (multi drug transporter regulated by LadR) in wild type *L. monocytogenes* and the LadR mutant *L. monocytogenes* strain (DP-L5396).

The locations of the Tn917 insertions were determined by plasmid rescue, as described in (Camilli et al., 1990). Briefly, chromosomal DNA from a Tn917 insertion mutant was digested with XbaI, ligated at a DNA concentration of 5 μg/mL, and used to transform DH5α cells and plated on kanamycin containing agar plates. Plasmid DNA was isolated from transformants and sequenced using a primer for Tn917: CAATAGAGAGATGTCACCG (SEQ ID NO:05) (FIGS. 5 and 6).

*Listeria monocytogenes* DNA Arrays

Oligos for *L. monocytogenes* arrays were synthesized by the institute for genomic research (TIGR). The arrays were printed at the UCSF Center for Advanced Technology. W.t. *L. monocytogenes*, lmo2589:: Tn917, lmo1408:: Tn917, and lmo1745:: Tn917 mid-log cultures were filtered and frozen in liquid nitrogen. Bacteria were washed off the filter, and bacterial RNA was isolated using phenol-chloroform extraction.

Bacterial RNA was amplified using Ambion MessageAmp™ II Bacteria Prokaryotic RNA Kit. Microarrays were gridded using Genepix and SpotReader, and analyzed using Acuity. Genes that showed a 2 fold or greater difference from wild type gene expression were selected for further analysis. Each sample was done in duplicate.

Example 2

Figure 7:
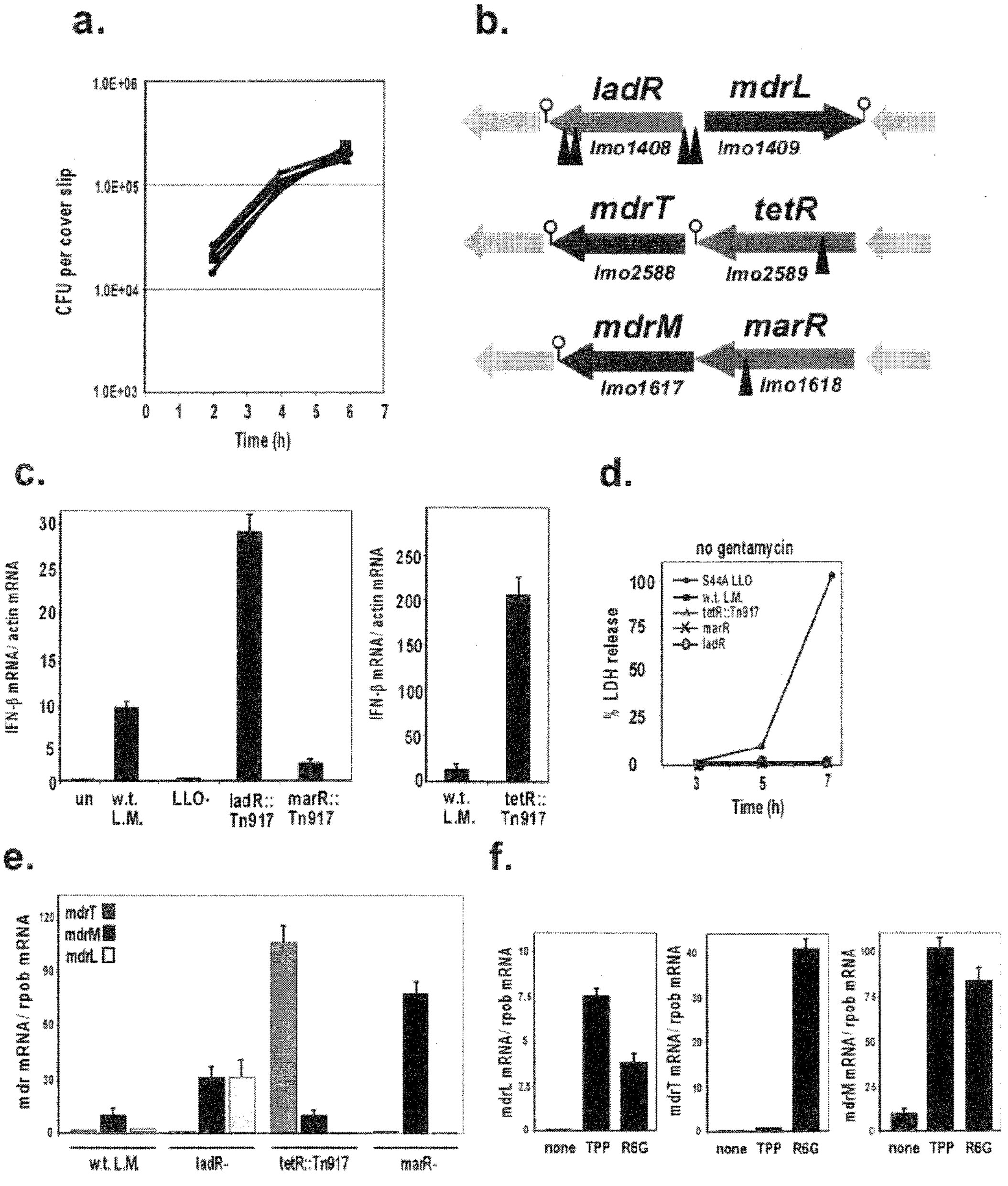
FIG. 7. includes graphs and a schematic diagram showing that *L. monocytogenes* strains with mutations in regulators of multidrug resistance transporters induce altered host IFN-β responses. a. Intracellular growth curves of w.t. *L. monocytogenes* (■), ladR::Tn917 (▲), tetR::Tn917 (●), and marR::Tn917 (•), in bone marrow derived macrophages (BMM) (Portnoy et al., ibid). b. Schematic presentation of site of transposon insertions (marked with triangles), mapped to genes predicted to be transcription regulators. c. Quantitative RT-PCR (qRT-PCR) analysis of IFN-β gene induction in BMM in response to infection with w.t. *L. monocytogenes*, ladR::Tn917, tetR::Tn917, and marR::Tn917. d. Lactate dehydrogenase (LDH) release assay was performed on macrophages infected with w.t. *L. monocytogenes*, tetR::Tn917, marR and LadR mutants at various time points post infection. *L. monocytogenes* cytotoxic LLO mutant S44A (Decatur, A. L. & Portnoy, D. A. A PEST-like sequence in listeriolysin O essential for *Listeria monocytogenes* pathogenicity. Science 290, 992-5 (2000); Schnupf, P. et al. Regulated translation of listeriolysin O controls virulence of *Listeria monocytogenes*. Mol Microbiol 61, 999-1012 (2006)) was used as a positive control. e. qRT-PCR analysis of *L. monocytogenes* MDR transporters expression in w.t. bacteria, ladR−, tetR::Tn917, and marR-mutants grown to mid-log in BHI broth. f. qRT-PCR analysis of MDRs expression by w.t. *L. monocytogenes* in the presence of the toxic compounds tetraphenylphosphonium (TPP) or rhodamine 6G (R6G). All error bars in FIG. 7 represent one standard deviation; n=2 or 3.

*Listeria Monocytogenes* Multidrug Resistance Transporters Activate a Cytosolic Surveillance Pathway of Innate Immunity To address the question of how *L. monocytogenes* activates the host cytosolic surveillance system, a *L. monocytogenes* Tn917 transposon library (Camilli et al. J Bacteriol 172, 3738-44 (1990)) was screened for mutants that exhibited an enhanced or diminished Type I IFN response upon infection of macrophages. Approximately 5000 *L. monocytogenes* Tn917 mutants were used to infect bone marrow derived macrophages (BMM) in 96 well plates. The amount of Type I interferon (i.e. IFN-β and/or IFN-α) secreted by macrophages during infection was measured by transferring macrophage culture supernatant onto a Type I interferon reporter cell line, that produces luciferase in response to Type I interferon (Jiang et al. Nat Immunol 6, 565-70 (2005)). 14 mutants that induced altered induction of Type I interferon in comparison to w.t. bacteria were identified. Among these, three mutants behaved like w.t. in their ability to infect, escape from the vacuole, and to grow inside macrophages (FIG. 7*a*). Transposon insertions in these mutants were located in genes encoding predicted transcription regulators (FIG. 7*b*): ladR, previously shown to be a negative regulator of its adjacent multidrug resistance transporter, MdrL (Huillet et al. FEMS Microbiol Lett 254, 87-94 (2006)), lmo2589 encoding a TetR-like protein and lmo1618 encoding a MarR-like protein (Grkovic et al. Proc Natl Acad Sci USA 98, 12712-7 (2001)). Real-time qRT-PCR analysis of IFN-β induction in macrophages infected with these mutants confirmed that the ladR mutant induced 3-fold more IFN-β, the tetR mutant induced 20-fold more IFN-β, and the marR mutant induced 3-fold less IFN-β compared to the level of IFN-β induced by w.t. bacteria (FIG. 7*c*). While the 3 mutants affected the level of IFN-β in macrophages, none of them induced macrophage cell death as shown by a lactate dehydrogenase (LDH) release assay (FIG. 7*d*). Interestingly, the $LD_{50}$ of ladR, tetR and marR mutants were similar to w.t. *L. monocytogenes* (data not shown). Since these mutants had the same $LD_{50}$ and grew like w.t. in macrophages, these mutants would have been missed in screens that rely on intracellular growth or virulence such as signature tag mutagenesis (STM) or transposon site hybridization (TraSH) (Sassetti et al. Proc Natl Acad Sci USA 98, 12712-7 (2001); Hensel et al. Science 269, 400-3 (1995)).

This is the first description of the tetR and marR genes in *L. monocytogenes*. Interestingly, like the ladR transcription regulator, the tetR and marR regulators are located adjacent to putative multidrug resistance transporters of the major facilitator superfamily, named here mdrT and mdrM respectively (lmo2588, lmo1617) (FIG. 7*b*). Among the 3 MDRs, MdrM and MdrT are highly similar (46% amino-acid identity and 64% similarity) and share extensive similarity with the well-studied multidrug efflux transporter system, QacA-QacR, of *Staphylococcus aureus* (Grkovic et al. Proc Natl Acad Sci USA 98, 12712-7 (2001)). In *S. aureus*, QacR represses expression of the MDR qacA. In order to study the regulation of mdrL, mdrT, and mdrM expression by their adjacent regulators and their effect on the cytosolic innate immune response, a series of in-frame deletions (Camilli et al. Mol Microbiol 8, 143-57 (1993)) of the regulator genes, the MDR genes, and a double deletion of each MDR-regulator set of genes was generated (Table 2), with the exception of the tetR gene, for which the original transposon tetR::Tn917 mutant was used. Table 2 lists the *Listeria monocytogenes* strains used in this study. Listed for each strain is the relative level of IFN-β induced by host macrophages, compared to the level of IFN-β induced by w.t. *L. monocytogenes*.

TABLE 2

| *L. monocytogenes* Strain | Description | IFN-β induction/w.t. *L. monocytogenes* |
|---|---|---|
| 10403S | Wild type | 1 |
| DP-L5396 | ladR::Tn917 | 3 |
| DP-L5398 | marR::Tn917 | 0.3 |
| DP-L5397 | tetR::Tn917 | 20 |
| DP-L5449 | Wt 10403S + pLIV2:mdrT | 3.5 |
| DP-L5441 | ladR- | 3 |
| DP-L5442 | marR- | 6 |
| DP-L5443 | mdrM- | 0.3 |
| DP-L5448 | mdrM- + pLIV2:mdrM | 1 |
| DP-L5444 | mdrT- | 1 |
| DP-L5445 | mdrL- | 1 |
| DP-L5446 | marR-/mdrM- | 0.3 |
| DP-L5447 | ladR-/mdr L- | 3 |

The expression level of each MDR was analyzed in bacteria grown in broth by real-time qRT-PCR. The results indicated that w.t. *L. monocytogenes* did not express mdrL or mdrT, but expressed a measurable level of mdrM (FIG. 7*e*). In the ladR-mutant the multidrug transporter mdrL was highly induced (~30 fold) (Huillet et al. FEMS Microbiol Lett 254, 87-94 (2006)). In addition, mutation in the ladR gene resulted in ~3 fold induction of mdrM, compared to its basal level of expression (FIG. 7*e*). In the tetR::Tn917 mutant the adjacent multidrug transporter, mdrT, was specifically and highly induced (~100 fold) (FIG. 7*e*). In the case of the marR-regulator, the mdrM gene was located downstream of marR, and both genes were predicted to be part of an operon (FIG. 7*b*). While mdrM was not expressed in the original marR::Tn917 mutant (not shown), it was highly induced in the marR in-frame deletion (~70 fold) (FIG. 7*e*), indicating that the transposon insertion blocked the expression of both genes due to polarity. These results clearly demonstrate that LadR, TetR and MarR negatively regulate the putative MDRs MdrL, MdrT and MdrM, respectively.

One common property of MDRs is that their expression is often induced by the presence of their cognate drug substrates. For example, in the QacA-QacR system, the repression of qacA imposed by QacR is relieved when QacR binds toxic drugs, leading to induction of qacA expression (Grkovic et al. Proc Natl Acad Sci USA 98, 12712-7 (2001); Schumacher et al. Mol Microbiol 45, 885-93 (2002)). When w.t. *L. monocytogenes* was grown in the presence of the commonly used toxic drugs, tetraphenylphosphonium (TPP) or rhodamine 6G (R6G) (Grkovic et al., ibid), the transcription of all 3 MDRs were highly induced (FIG. 7*f*), indicating that the regulator genes identified in this screen are involved in the regulation of MDR transporters.

Figure 8:
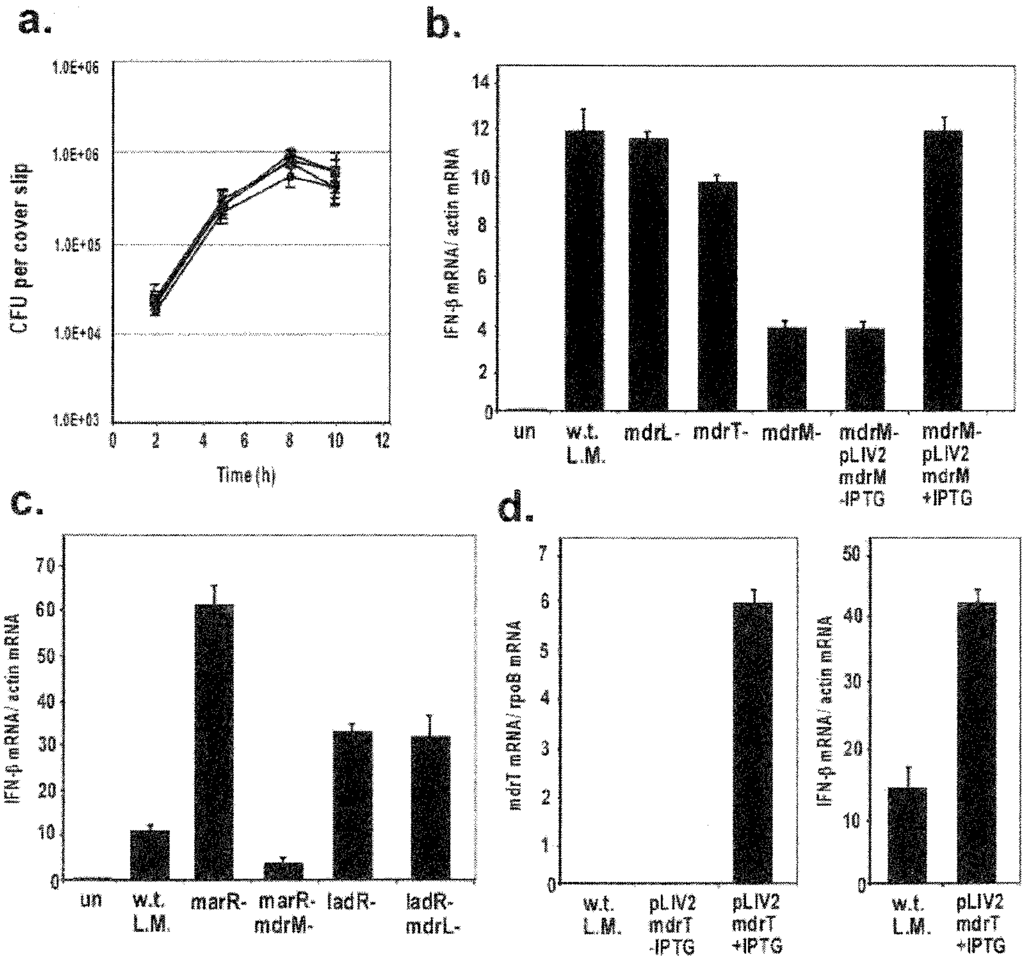
FIG. 8: includes graphs showing the role of the *L. monocytogenes* MDR transporters mdrL, mdrT, and mdrM in the induction of IFN-β from macrophages. a. Intracellular growth curves of w.t. *L. monocytogenes* (●) and the deletion mutants: mdrL− (■), mdrT− (x), and mdrM− (♦) in BMMs (Portnoy et al., ibid.). b. qRT-PCR analysis of IFN-fβ induction in BMMs infected with w.t. *L. monocytogenes*, mdrL−, mdrT−, mdrM−, and a complemented mdrM-strain expressing mdrM from the IPTG inducible vector pLIV2 (Fischetti et al., ibid.) c. qRT-PCR analysis of IFN-β induction in BMMs infected with ladR−, marR− or the double deletions of ladR−/mdrL− or marR/mdrM−. d. qRT-PCR analysis of mdrT expression level in w.t. *L. monocytogenes* bacteria containing IPTG-inducible plasmid pLIV2::mdrT, and analysis of IFN-β induction by this strain in infected BMMs. All error bars in FIG. 8 represent one standard deviation; n=2 or 3.

Prior to this disclosure, nothing was known about the regulation of MDR transporters during *L. monocytogenes* infection. For example, it was not clear whether the bacteria encounter toxic compounds during infection that might lead to induction of the MDRs. When macrophages were infected with strains deleted for each of the MDR transporters (mdrL, mdrT and mdrM) all 3 mutants were able to infect and replicate within macrophages like w.t. bacteria (FIG. 8*a*). In order to evaluate role(s) of these MDRs in the induction of type I interferon, macrophages were infected with w.t. *L. monocytogenes* and the MDR mutants, and the induction of IFN-β was analyzed at 4 hours post infection by real-time qRT-PCR. The results clearly demonstrated that among the 3 MDRs. MdrM was the only one necessary for induction of IFN-β, as this mutant induced only a third of the IFN-β induced by w.t. bacteria (FIG. 8*b*). This result is consistent with the observation that only mdrM exhibits basal expression in w.t. *L. monocytogenes* (FIG. 7*e*). Complementation of mdrM expression with an IPTG-inducible expression system (pLIV2 integration vector) (Fischetti et al. Gram-positive pathogens. ASM Press, Washington, D.C., (2006)) restored the induction of IFN-β to the level induced by w.t. bacteria (FIG. 8*b*). The marR deletion mutant, which overexpressed mdrM (FIG. 7*e*), induced 6-fold more IFN-β than w.t. bacteria (FIG. 8*c*). This level of IFN-β induction was completely dependent on mdrM expression since it was not observed with the marR-mdrM double deletion mutant, which induced the same level of IFN-β as the mdrM mutant alone, thereby excluding a potential role for other MarR inducible genes (FIG. 8*c*). Further support for the role of MdrM in IFN-β induction came from infecting macrophages with the ladR mutant. As shown in FIG. 7*e*, LadR also repressed the expression of mdrM, to a lesser extent than the MdrM-repressor. Infecting macrophages with the ladR-mutant resulted in a 3 fold higher induction of IFN-β than with w.t. bacteria; however, infection with the double deletion ladR-mdrL mutant still induced 3 fold more IFN-β then w.t. bacteria, indicating that this induction was not due to over-expression of mdrL (FIG. 8*c*). Microarray analysis comparing total gene expression of w.t. bacteria versus the ladR mutant revealed that, besides mdrL, mdrM was the most differentially expressed gene in the ladR-mutant (Table 3). Table 3 shows the results of microarray analysis comparing total gene expression of w.t. vs. ladR::Tn917 *L. monocytogenes*. RNA was isolated from bacteria grown to mid-log culture in Brain Heart Infusion media. All microarrays were done in duplicate, and the values shown are the average of 2 arrays, divided by wild type bacteria. All genes that showed a 2 fold difference vs. wild type bacteria are presented. Since mdrM over-expression in the marR-mutant resulted in enhanced host IFN-β expression (FIG. 7*e*, 8*c*), the induction of IFN-β by the ladR-mutant was due to over-expression of mdrM and not mdrL. Overall, these results demonstrated a direct role for MdrM in activation of IFN-β in response to *L. monocytogenes* infection. Interestingly, w.t bacteria expressing IPTG-inducible MdrT (MdrM homolog) also resulted in increased induction of IFN-β in infected macrophages (FIG. 8*d*) (Fischetti et al., ibid). These observations indicate that the induction of IFN-β was not restricted to MdrM, but could be recapitulated by expression of homologous MDRs, likely with similar substrate specificity.

TABLE 3

| Gene number | Fold Expression/Wt |
|---|---|
| lmo 1409 (mdrL) | 164.3 |
| lmo 1617 (mdrM) | 3.26 |
| lmo 2434<br>hypothetical protein<br>(similar to glutamate<br>decarboxylase) | 3.21 |
| lmo 1069<br>hypothetical protein<br>(similar to *B. subtilis* YlaI protein) | 3.16 |
| lmo 2443<br>hypothetical protein | 2.30 |

TABLE 3-continued

| Gene number | Fold Expression/Wt |
|---|---|
| lmo 2840<br>hypothetical protein<br>(similar to Sucrose phosphorylase) | 2.18 |
| lmo 1308<br>hypothetical protein<br>(similar to arginine N-<br>methyltransferases) | 0.39 |

To determine whether the lethality of the ladR, tetR and mdrM (pump1617) mutant strains was distinguishable from that of the wild type *L. monocytogenes*, the 50% lethality dose ($LD_{50}$) for the three strains were determined in Balb/c mice. Table 4 shows the results, which indicate that the $LD_{50}$ of the mutant strains are similar to those of the wild type.

TABLE 4

| Strain | Study AS07-023 | Study AS07-029 |
|---|---|---|
| WT | $<7 \times 10^3$ | $1.39 \times 10^4$ |
| ladR | $6.90 \times 10^3$ | $1.27 \times 10^4$ |
| tetR | $1.40 \times 10^4$ | $1.54 \times 10^4$ |
| Pump1617 (mdrM) | $2.34 \times 10^4$ | $>8 \times 10^4$ |

Figure 12:
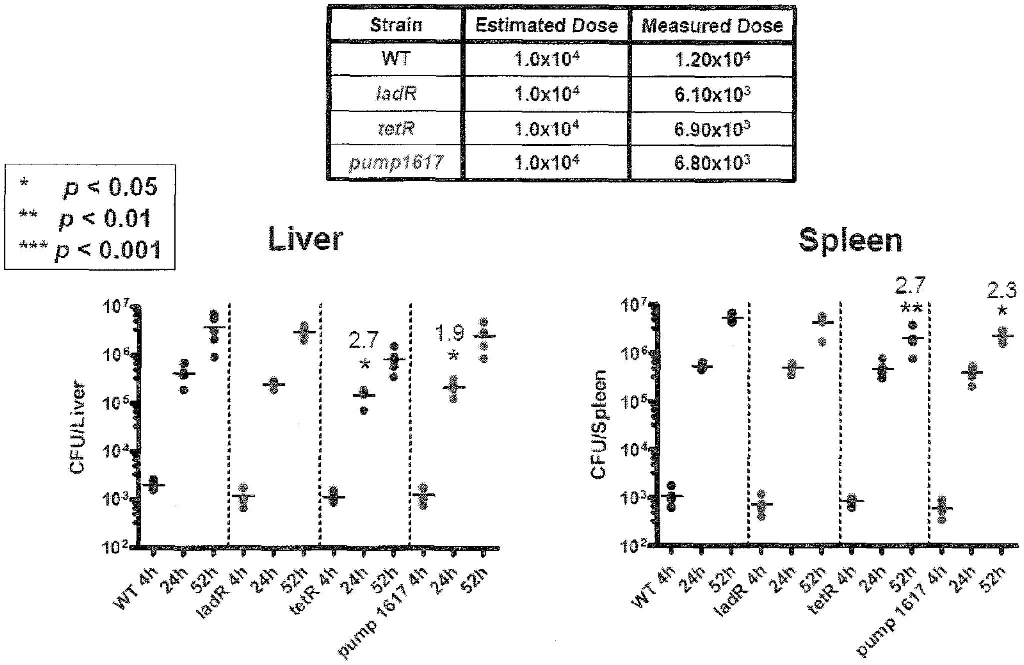
FIG. 12: includes graphs showing the results of the 52 hour time course, indicating that tetR and pump1617(mdrM) mutants are slightly attenuated at 24 h in the liver and 52 h in the spleen.

To study the biodistribution of the ladR, tetR and mdrM mutant strains, 52 hour as well as 10-day time courses examining liver and spleen colonization in Balb/c mice were conducted as described previously by Auerbuch, V. et al, Infect. Immun. 69:5953-5957. FIG. 12 shows the results of the 52 hour time course, which indicate that tetR and pump1617 (mdrM) mutants are slightly attenuated at 24 h in the liver and 52 h in the spleen.

Figure 9:
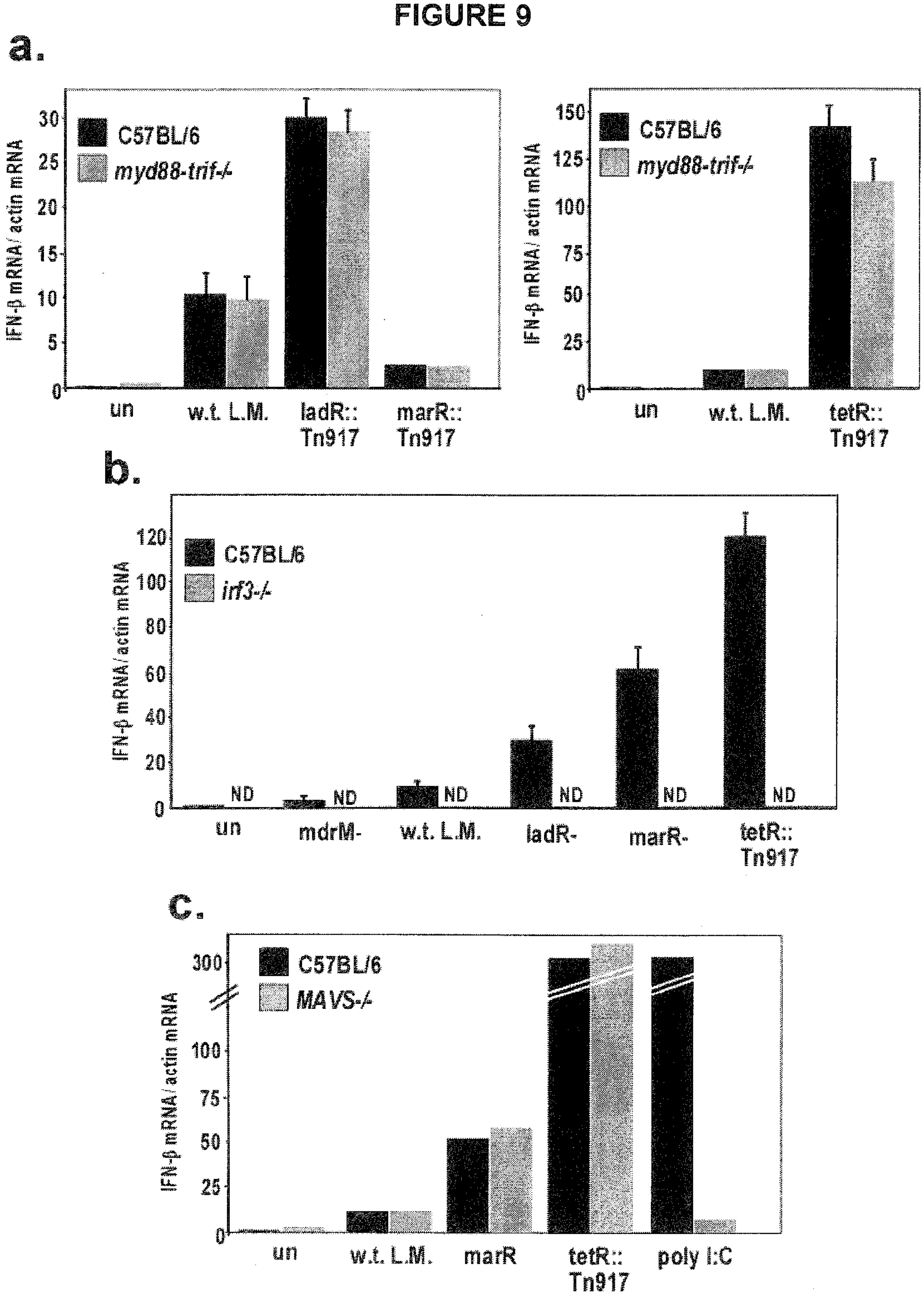
FIG. 9: includes graphs showing that induction of IFN-β by ladR, tetR, and marR mutants is independent of MyD88/Trif and MAVS but dependent on IRF-3. qRT-PCR analysis of IFN-β induction in C57BL/6 w.t. vs. myd88/trif−/− BMMs (a.), and C57BL/6 w.t. vs. irf3−/− BMMs (O'Connell et al., ibid) (b.) infected with w.t. *L. monocytogenes*, and ladR, marR, tetR regulator mutants. All error bars in FIG. 9 represent one standard deviation; n=2. c. qRT-PCR analysis of IFN-β induction in C57BL/6 BMMs vs. MAVS−/− BMMs (Sun, Q. et al. The specific and essential role of MAVS in antiviral innate immune responses. Immunity 24, 633-42 (2006)) infected with w.t. *L. monocytogenes*, marR, tetR-Tn917 mutants, or transfected with poly [I:C] as a positive control.

Prior to this disclosure, how immune cells recognize intracellular pathogens such as *L. monocytogenes* was not fully understood. The cytosolic innate immune response to *L. monocytogenes* is generally described as independent of Toll-like receptors (TLRs) and their signaling adaptors, Myd88 and Trif, and dependent on the interferon regulatory factor 3 (IRF-3) (Perry et al. Cell Res 15, 407-22 (2005)). In order to test whether induction of IFN-β by the mutants identified in this screen activated the same pathway, Myd88-Trif double knockout macrophages and IRF-β deficient (O'Connell et al. J Exp Med 200, 437-45 (2004)) macrophages were infected with ladR, marR, and tetR mutants. The results indicated that the increased induction of IFN-β by these mutants was almost entirely independent of TLRs but absolutely dependent on IRF-3 (FIG. 9). One well-characterized cytosolic pathway that leads to IRF-β activation and IFN-β expression is dependent on the cytosolic receptors RIG-I and MDA-5 and their adaptor, MAVS (Yoneyama, M. et al. Nat Immunol 5, 730-7 (2004); Andrejeva, J. et al. Proc Natl Acad Sci USA 101, 17264-9 (2004); Sun, Q. et al., ibid). We infected MAVS deficient macrophages with w.t. *L. monocytogenes*, marR, and tetR::Tn917 mutants, and the induction of IFN-β by w.t. *L. monocytogenes* and the mutants was independent of MAVS (Sun, Q. et al., ibid; Soulat, D., et al. Cytoplasmic *Listeria monocytogenes* stimulates IFN-beta synthesis without requiring the adapter protein MAVS. FEBS Lett 580, 2341-2346 (2006)). These results are consistent with the hypothesis that w.t. *L. monocytogenes* and the mutants induced altered levels of activation of the same host cytosolic surveillance pathway. To gain further insight into the host pathways and downstream genes activated by bacterial MDRs, we compared the macrophage response to infection with w.t. *L. monocytogenes*, mdrM- and tetR::Tn917 mutants using microarray analysis. We used Type I IFN Receptor minus (IFNαβR−/−) macrophages to avoid the complication of IFN-β autocrine signaling. Macrophages infected with the mdrM-mutant, which induced a 3 fold lower host IFN-β response, had altered expression of only 16 genes (by SAM analysis), all of which were diminished compared to macrophages infected with w.t. *L. monocytogenes*. Macrophages infected with the tetR::Tn917 mutant, which induced a 20 fold higher IFN-β response, had strongly increased induction (by SAM and at least 4 fold) of 13 genes, compared to macrophages infected with w.t. *L. monocytogenes*. Interestingly, the genes whose expression was affected by mdrM- and tetR::Tn917 mutants largely overlapped and are presented in FIG. 4. Moreover, the vast majority of these genes were previously identified as "cytosolic response genes" (i.e. genes that are induced only by w.t. *L. monocytogenes* in the cytosol) and included IFN-β, IL-6, CCL5, and CXCL10 (Leber, J. et al. Distinct TLR- and NLR-Mediated Transcriptional Responses to an Intracellular Pathogen. PLoS Pathogens, In press (2007)). These experiments provided further evidence that bacterial MDR expression specifically controlled the magnitude of the host cytosolic surveillance pathway, including the expression of several innate immune signaling components.

To test the role of the cytosolic surveillance pathway in *L. monocytogenes* pathogenesis, we infected mice with w.t. *L. monocytogenes*, mdrM-, marR-, and tetR::Tn917 mutants. Interestingly, mice infected with the mutant that induced 20 times more IFN-β, tetR::Tn917, had 20-fold lower bacterial loads in the liver, while the other mutants had w.t. levels of bacteria (FIG. 11*a*). While *L. monocytogenes*' virulence may require basal activation of the cytosolic surveillance system (Auerbuch et al., ibid) our new data are more consistent with a model in which *L. monocytogenes* avoids recognition by the host innate immune surveillance system.

Figure 11:
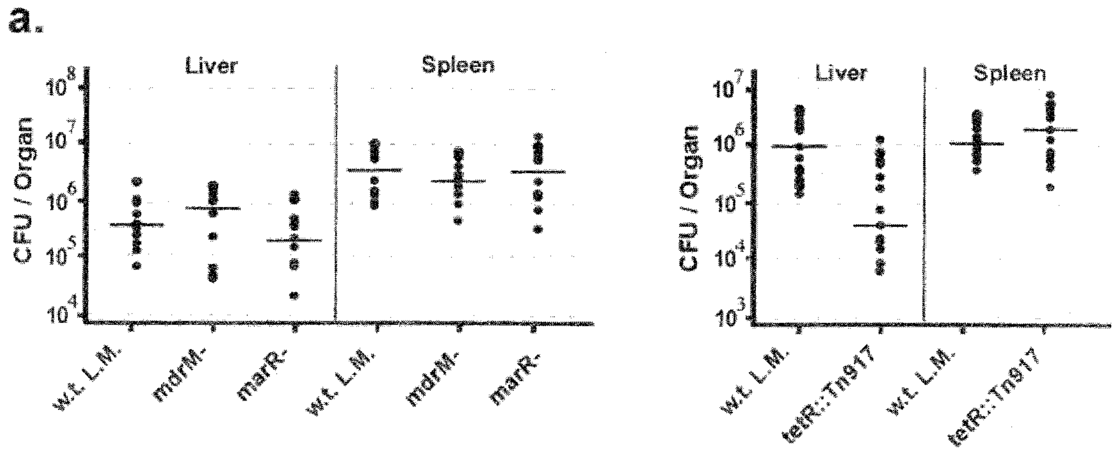
FIG. 11: includes a graph showing liver and spleen colonization by mutant strains and induction of IFN-β in vivo by ladR, tetR, and marR transposon mutants. a. C57BL/6 mice were infected with $1\times10^4$ (0.1 LD50) of w.t., mdrM-, marR-, or tetR::Tn917 *L. monocytogenes*. Organs were collected 48 hours post infection, and bacterial numbers are represented as colony forming units (cfu) per organ. b. Detection of Type I IFN levels in serum of Balb/C mice infected intravenous ($1\times10^4$ bacteria) with Hank's Buffered Salt Solution (HBSS), w.t. *L. monocytogenes*, ladR::Tn917, tetR::Tn917, or marR::Tn917 for 24 hours. Units are presented as relative light units (RLU), detected by luciferase reporter ISRE-L929 cell line assay (Jiang et al., ibid). For each strain, n=5 mice, and the median value is represented by a horizontal line.
Figure 11:
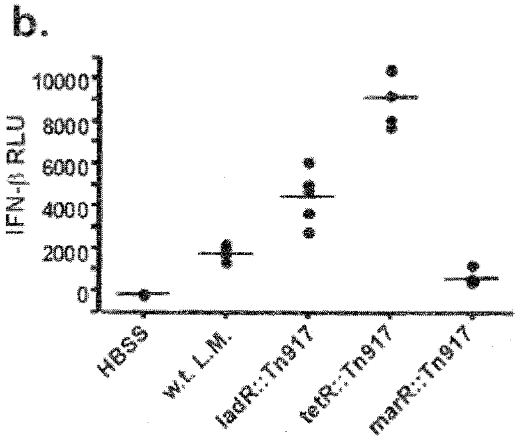

This disclosure is the first report to demonstrate a role for bacterial MDR transporters in the activation of a host immune response. *L. monocytogenes* strains were generated that vary by 60-fold in the amount of IFNβ induced in infected macrophages, due to their levels of MDR expression (FIG. 9*b*). Importantly, the induction of IFNβ in infected animals recapitulated the results observed in tissue culture (FIG. 11). Type I interferons have wide ranging effects on innate and adaptive immune responses, and are used to treat multiple sclerosis, hepatitis C, and some malignancies (Theofilopoulos et al. Annu Rev Immunol 23, 307-36 (2005); Maher et al. Curr Med Chem 14, 1279-89 (2007)). The strains generated in this study can be used to provide novel insight into the role of IFN-β in linking innate and adaptive immunity, as well as being instrumental in the development of adjuvants and vaccines, and of use in new therapeutics.

Methods Summary:

Bacterial Genetic Screen.

A total of 5000 individual *L. monocytogenes* Tn917-LTV3-transposon insertion mutants (Camilli et al. J Bacteriol 172, 3738-44 (1990)) were grown on BHI media in 96 well plates over night at 30° C. Bone marrow-derived macrophages from C57BL/6 mice were plated on 96 well plates, $4\times10^4$ cells/well, and infected with $2\times10^6$ bacteria. 30 minutes post infection, macrophages were washed and gentamicin was added (50 μg/ml) to prevent extracellular growth of bacteria. At 6 hours post infection 100 μl of macrophage culture media was taken and frozen at −80. The amount of Type I IFN in the media was detected using a reporter cell line, ISRE-L929 (Jiang et al. Nat Immunol 6, 565-70 (2005)). ISRE-L929 cells were grown in 96 well plates and incubated with 40 μl of infected macrophage culture media for 4 h. Then, cells were lysed and luciferase activity was detected using Bright Glow Assay (Promega, E-2620) and measured with a luminescence counter (VICTOR3, PerkinElmer®).

Determination of Type I Interferon Level in Mice Serum.

Balb/C mice were injected intravenous with either HBSS alone or $1\times10^4$ cfu of each bacterial strain in 100 μl of HBSS. 24 h. later, mice were sacrificed and blood was collected to serum separator tubes (BD 39 5956) by cardiac puncture. Serum was aliquotted and frozen at −80° C. until it was used to assay Type I interferon in the ISREL929 reporter cell line as described above. Assays were performed in duplicate.

Infections and Analysis of Gene Expression in Macrophages.

RNA was collected from infected macrophages at 4 hours post infection, and induction of IFN-β was analyzed by qRT-PCR, as described 20.

*Listeria Monocytogenes* Gene Expression.

Expression of MDR genes by *L. monocytogenes* growing in BHI broth was analyzed using real time qRT-PCR analysis (Herskovits et al. PloS Pathog 3, e51 (2007)). Level of gene expression was normalized to the level of expression of rpoB gene. To test for expression of MDR genes after treatment with toxic drugs, Tetraphenylphosphonium (50 μM, Sigma) or Rhodamine 6G (50 μM, Sigma) were added for 1 hour, then total bacteria RNA was extracted and analyzed by qRT-PCR (Herskovits et al., ibid).

Bacterial Strains.

The *L. monocytogenes* strains used were a wild-type strain, 10403S, or a strain containing an in-frame deletion of the hly gene (LLO, DP-L2161) (Jones et al. Infect Immun 62, 5608-13 (1994)). All deletion mutants generated in this study are summarized in Table 3.

Source of Mice.

C57BL/6 and Balb/C mice were obtained from The Jackson Laboratory and Charles River respectively. Unless indicated otherwise all knockout mice used in this 11 study were on the C57BL/6 background. Femurs or mice were obtained from the following source: MyD88Trif−/−, from B. Beutler, The Scripps Research Institute, La Jolla; IRF3−/− from G. Cheng, Department of Microbiology, Immunology and Molecular Genetics, University of California.

Bacterial Genetic Screen.

*L. monocytogenes* Tn917-LTV3-transposon insertion libraries were used for the screen (Camilli et al. J Bacteriol 172, 3738-44 (1990)). A total of 5000 bacterial insertion mutants were grown on BHI media in 96 well plates and were grown overnight at 30° C. without shaking. Bone marrow-derived macrophages from C57BL/6 mice were plated on 96 well plates, $4\times10^4$ cells/well and were infected, in triplicate, with $2\times10^6$ bacteria. Half an hour post infection, macrophages were washed to remove extracellular bacteria and gentamicin was added at a concentration of 50 μg/ml to prevent extracellular growth of bacteria. At 4 hours post infection 100 μl of macrophages culture media was taken and frozen at −80. The amount of Type I IFN secreted by macrophages during bacterial infection was detected using the reporter gene luciferase, cloned under the regulation of Type I interferon signaling pathway in L929 cell line, ISRE-L929 (Jiang et al., ibid.). ISRE-L929 cells were grown in 96 well plates and were incubated with 40 μl of infected macrophages culture media for 4 h. Then, cells were lysed and luciferase activity was detected using Bright Glow Assay (Promega, E-2620) and light emission measurement by luminescence counter (VICTOR3, PerkinElmer®. Screening of mutants was done in triplicate for each mutant on the same plate and 8 replicates of w.t. *L. monocytogenes* and hly-minus mutant as controls.

Generation of in-Frame Deletion Mutants in *L. Monocytogenes*.

In-frame deletions of *L. monocytogenes* genes were generated using splice-overlap extension (SOE)-PCR and allelic exchange, as previously described by Camilli et al (Camilli et al. Mol Microbiol 8, 143-57 (1993)). LD50 study. Pathogenicity was determined in 5-6 week old BALB/C mice by serial twofold dilutions of each bacterial strain. LD50 calculations were done by the method of Reed and Muench (Reed et al. The American Journal of Hygiene 27, 493-497 (1938)).

Determination of Type I Interferon Level in Mice Serum.

BALB/C mice were injected intravenously with either HBSS alone or $1\times10^4$ cfu of each bacterial strain in 100 μl of HBSS. Titers were confirmed by plating injection stocks for cfu counting. 24 h later, mice were sacrificed and blood, collected by cardiac puncture, was placed in serum separator tubes (BD 39 5956) and processed per manufacturer's recommendations. Serum was aliquotted and frozen at −80° C. until Type I interferon level could be assayed. 50 μl of serum was thawed and used to assay Type I interferon in the ISRE-L929 reporter cell line as described for the bacterial genetic screen (above). Assays were performed in duplicate.

Bacterial Intracellular Growth Curves.

Characterization of intracellular bacterial growth was performed using primary cultures of bone marrow derived macrophages as described (Portnoy et al. J Exp Med 167, 1459-71 (1988)). Briefly, $2\times10^6$ macrophages were infected with $4\times10^5$ *L. monocytogenes* from an overnight culture. Thirty minutes after addition of bacteria macrophage monolayers were washed with PBS. At one h.p.i., gentamicin was added to 50 μg $ml^{-1}$, to limit the growth of extracellular bacteria. At different time points post infection 3 cover slips were taken and washed with water to lyse macrophages cells. Bacteria recovered from each coverslip were plated on BHI plates and the number of bacterial colonies was counted.

Infections and Analysis of Gene Expression in Macrophages.

Approximately $8\times10^6$ *L. monocytogenes* were used to infect $2\times10^6$ macrophages cells seeded on 60 mm Petri dish. These numbers resulted in infection of 1-2 bacteria per cell. Thirty minutes after addition of bacteria, macrophage monolayers were washed three times with PBS and fresh media was added. At one hour post infection (h.p.i.), gentamicin was added to 50 μg $ml^{-1}$, to limit the growth of extracellular bacteria. Unless indicated otherwise, RNA was collected at 4 h.p.i for further analysis. Induction of IFN-β by macrophages analyzed by real time qRT-PCR as described (Herskovits et al., ibid.).

*Listeria Monocytogenes* Gene Expression.

Expression of MDR genes by *L. monocytogenes* grown in BHI broth was analyzed using real time qRT-PCR analysis (Herskovits et al., ibid.). Level of gene expression was normalized to the level of expression of rpoB gene in *L. monocytogenes*. Primers sequence: rpoB F (SEQ ID NO: 6): gcggatgaagaggataattacg; rpoB R (SEQ ID NO: 7): ggaatccatagatggaccgtta; mdrL F (SEQ ID NO: 8): gggaaatggataacagcggc; mdrL R (SEQ ID NO: 9): gagcattgtcatcgcgg; mdrM F (SEQ ID NO: 10): ggtattttgattgttatgcttatgg; mdrM R (SEQ ID NO: 11): ttgtaaatcgttcaattaaaaaggc; mdrT F (SEQ ID NO: 12): aatagtacagcagtagaacg; mdrT R (SEQ ID NO: 13): ctgtaatatgcaaatcatcc. To test for induction of MDR expression in the presence of toxic drugs, an over-night culture of w.t. *L. monocytogenes* was diluted to O.D.600 of 0.01 and grown to mid-log in BHI media at 37 C shaking. Tetraphenylphosphonium (50 μM, Sigma) and Rhodamine 6G (50 μM, Sigma) were added for 1 hour and than bacteria were harvested, and total bacteria RNA was extracted and analyzed by qRT-PCR (Herskovits et al., ibid.).

Microarray Analysis of *L. Monocytogenes* Gene Expression.

Oligonucleotides for *L. monocytogenes* arrays were synthesized by the institute for genomic research (TIGR), and the arrays were printed at the UCSF Center for Advanced Technology. Midlog cultures of w.t. *L. monocytogenes* and ladR::Tn917 mutants were filtered and frozen in liquid nitrogen. Bacteria were washed off the filter, and bacterial RNA was isolated using phenol-chloroform extraction. Bacterial RNA was amplified using MessageAmp™ II Bacteria Prokaryotic RNA Kit (Ambion). Microarrays were gridded using Genepix and SpotReader, and analyzed using Acuity software (Herskovits et al., ibid.). Genes that showed a 2-fold or greater difference from w.t. gene expression were selected for further analysis. Each sample was done in duplicate.

Microarray Analysis of w.t. *L. Monocytogenes*, mdrM−, and tetR::Tn917 Infected IFNαβR Deficient Macrophages.

Figure 10:
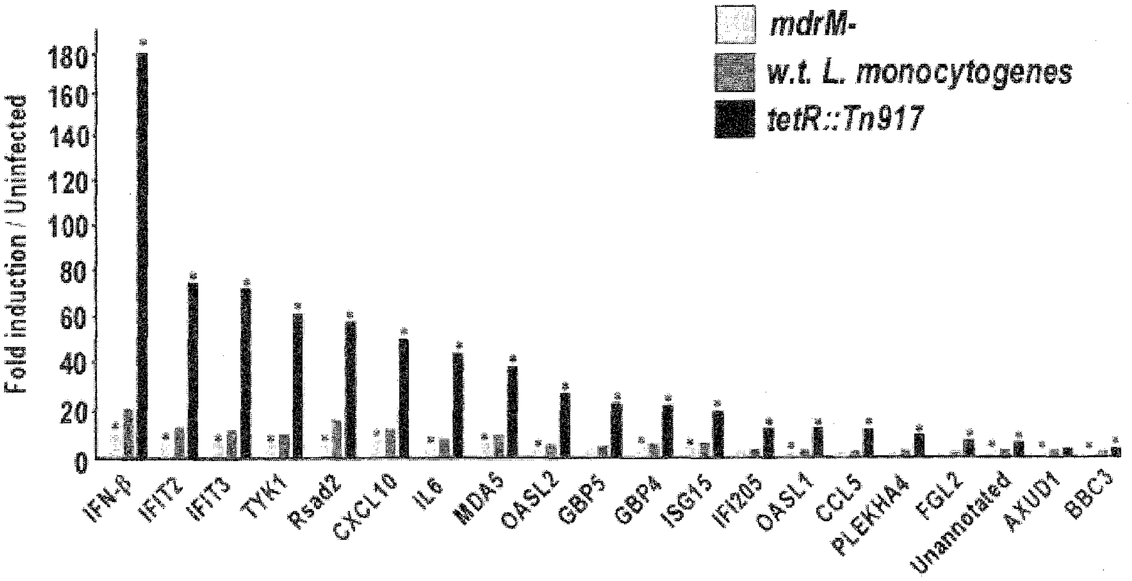
FIG. 10: includes a graph showing that *L. monocytogenes* MDR expression determines the magnitude of the host immune response. Genes identified, by microarray analysis, as having lower expression in mdrM-infected IFNαβR−/− macrophages (by SAM) or higher expression in tetR::Tn917 infected IFNαβR−/− macrophages (by SAM and at least 4 fold higher than Wt), as compared to their expression in w.t. *L. monocytogenes* infected IFNαβR−/− macrophages. All data is represented as fold induction over uninfected macrophages, and is the average of 2 experiments. The (*) symbol indicates that these values are significantly different from macrophages infected with w.t. *L. monocytogenes*, by SAM analysis with a false discovery rate of 10%.

Microarray analysis of IFNαβR−/− macrophages infected with w.t. *L. monocytogenes*, mdrM−, or tetR::Tn917 mutants was done as previously described (Leber, J. et al., Distinct TLR- and NLR-Mediated Transcriptional Responses to an Intracellular Pathogen. PLoS Pathogens, In press (2007); Herskovits et al., ibid.), with the following modifications: 1) Macrophages were infected at MOI of 1, and RNA was collected 4 hours post infection. 2) After normalizing all microarrays to the uninfected controls, SAM analysis was performed with two-class unpaired designs to identify genes that were differentially expressed in w.t *L. monocytogenes* infected versus mdrM- or tetR::Tn917 infected macrophages, with a false discovery rate of 10%. Those genes that were statistically changed in mdrM-infected macrophages, and those genes that were statistically changed and at least 4 fold differentially expressed (from w.t. *L. monocytogenes*) in tetR::Tn917 infected macrophages were selected for further analysis (FIG. 10). Accession numbers for the genes in FIG. 10 are as follows: NM_010510 (IFNβ), NM_008332 (IFIT2), NM_010501 (IFIT3), NM_020557 (TYKI), NM_031168 (IL6), BC030067 (CXCL10), NM_027835 (MDA5), NM_021384 (Rsad2), NM_145209 (OASL1), NM_011854 (OASL2), NM_153564 (Gbp5), NM_018734 (Gbp3), NM_015783 (ISG15), NM_172648 (Ifi1205), NM_148927 (Plekh4), NM_008013 (Fgl2), NM_153287 (Axud1), and NM_133234 (Bbc3). The un-annotated gene is RIKEN cDNA 1190002H23.

Lactate Dehydrogenase (LDH) Release Assay.

BMMs macrophages were infected with w.t. *L. monocytogenes* and mutants at a multiplicity of infection (MOI) of one in the absence of gentamicin. Three, five and seven hours post infection, supernatant sample was removed and assayed for LDH activity. Reagents were purchased from Sigma. The numbers reported were calculated with the mean LDH release from three wells of a single experiment and are representative of two independent experiments. The *L. monocytogenes* cytotoxic strain S44A LLO was used as a positive control.

Example 3

*Listeria Monocytogenes* Mutants in a Multidrug Resistance Transporter Gene and Multidrug Resistance Transporter Gene Transcriptional Regulators Induce an Altered Type I Interferon Response Human type I interferons (IFNs) bind to a specific cell surface receptor complex known as the IFN-α receptor (IFNAR) that consists of IFNAR1 and IFNAR2 chains. Homologous molecules to type I IFNs are found in many species, including most mammals, and some have been identified in birds, reptiles, amphibians and fish species (Schultz et al., Developmental and Comparative Immunology, Volume 28, pages 499-508). IFN-α and IFN-β are secreted by many cell types including lymphocytes (natural killer (NK) cells, B-cells and T-cells), macrophages, fibroblasts, endothelial cells, osteoblasts and others. They stimulate both macrophages and NK cells to elicit an anti-viral response, and are also active against tumors.

Figure 13:
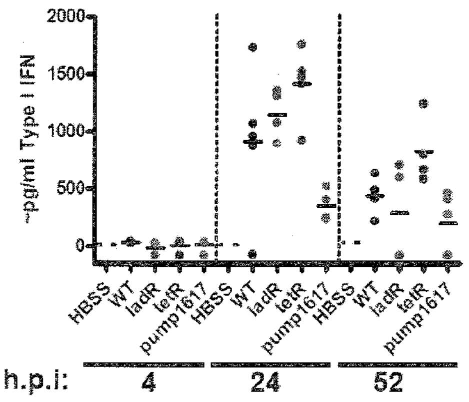
FIG. 13: includes a table and graphs indicating that tetR and ladR strains show elevated Type I IFN responses relative to w.t. *L. monocytogenes*.
Figure 13:
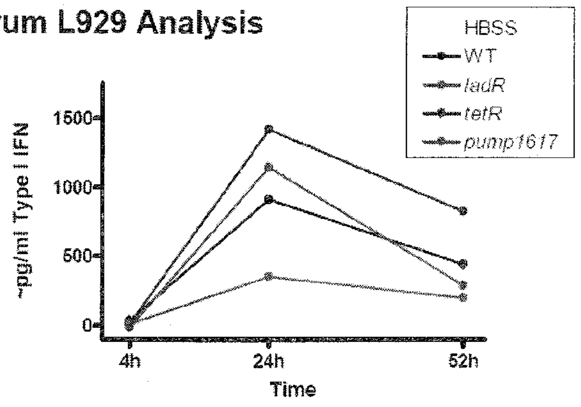

Mice lacking the type I interferon receptor are resistant to infection with wild type *L. monocytogenes*, producing high levels of IL-12 in lieu of IFN-αβ (Auerbuch et al., ibid). In addition to MHC and costimulatory molecule signaling, it has been documented that Type I IFNs provide a third signal to CD8+ T cells to stimulate effective clonal expansion and effector function. As such, modulation of Type I IFNs finds use in mounting a more effective adaptive immune response in vaccine platforms. To determine whether ladR, tetR and mdrM (pump1617) mutant strains induced Type I IFN responses differed from that of the wild type *L. monocytogenes*, L929 mouse fibroblast line (ATCC Cat. No. CCL-1) cells were exposed to serum from Balb/c mice infected with w.t., ladR, tetR and mdrM (pump1617) mutant strains. The results presented in FIG. 13 indicate that tetR and ladR strains show elevated Type I IFN responses relative to w.t. *L. monocytogenes*.

Figure 14:
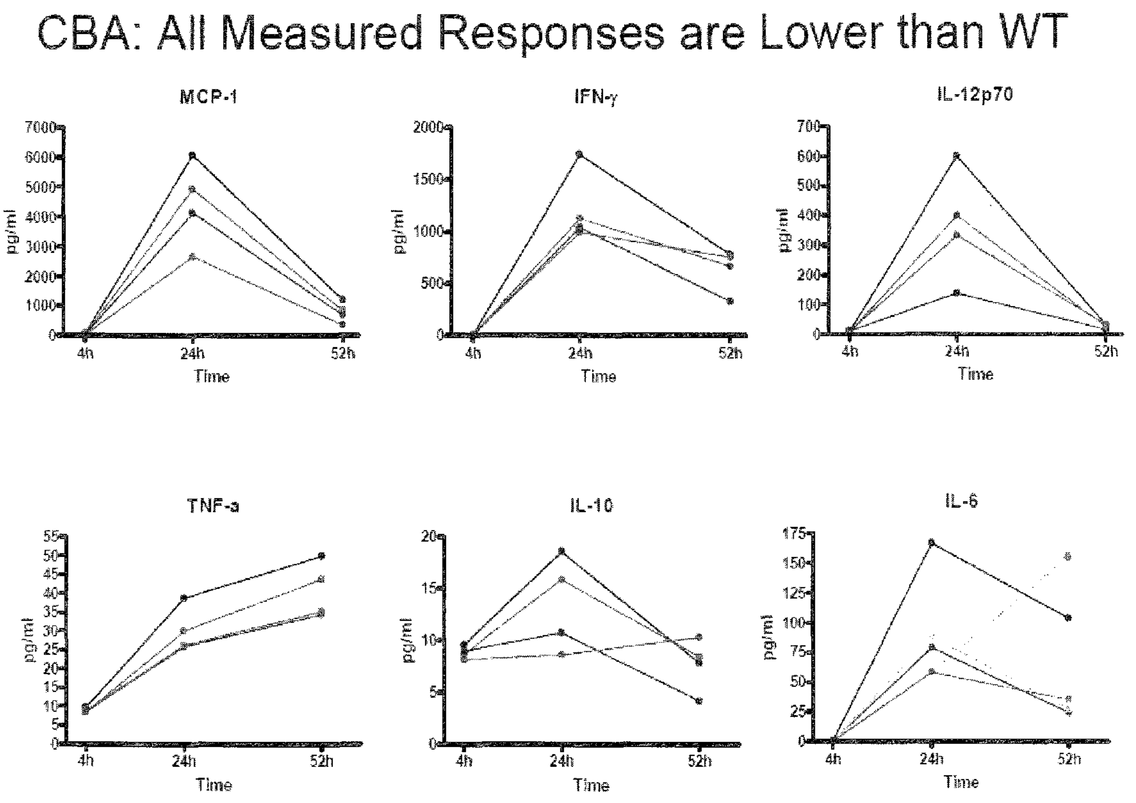
FIG. 14: includes graphs indicating that MCP-1, IFN-γ, IL-12p70, TNF-α, IL-10, and IL-6 secretion is lower for mutant than for w.t. *L. monocytogenes* strains.

To investigate the effects on secretion of other cytokines by infection with the ladR, tetR and mdrM (pump1617) mutant strains relative to w.t., cytometric bead array (CBA) assays were performed as described by Chen et al. (Chen R, Lowe L, Wilson J D, Crowther E, Tzeggai K, Bishop J E, et al., Simultaneous quantification of six human cytokines in a single sample using microparticle-based flow cytometric technology. Clin Chem 1999; 45:1693-1694) using serum from infected Balb/c mice. FIG. 14 shows the results, which indicate that MCP-1, IFN-γ, IL-12p70, TNF-α, IL-10, and IL-6 secretion is lower for all mutants.

Figure 15:
FIG. 15: shows a schematic and conditions for the natural killer (NK) cell activation assay of FIG. 16.
Figure 16:
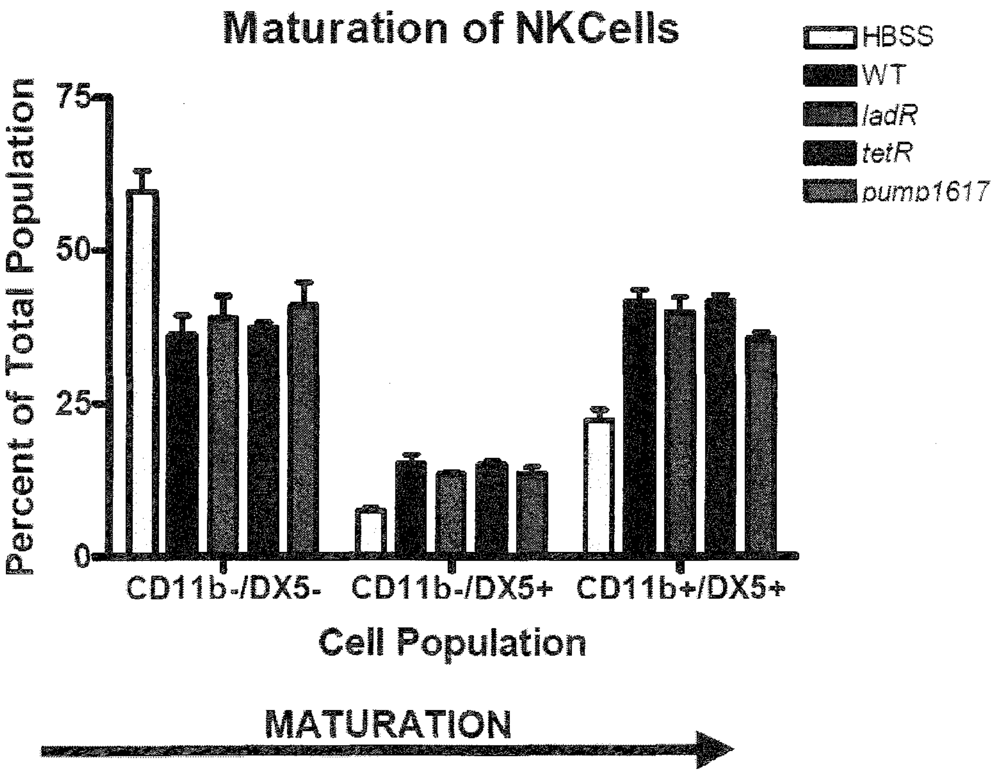
FIG. 16: includes a graph indicating that all *L. monocytogenes* strains, mutant and w.t., yielded similar liver NK cell maturation profiles.
Figure 17:
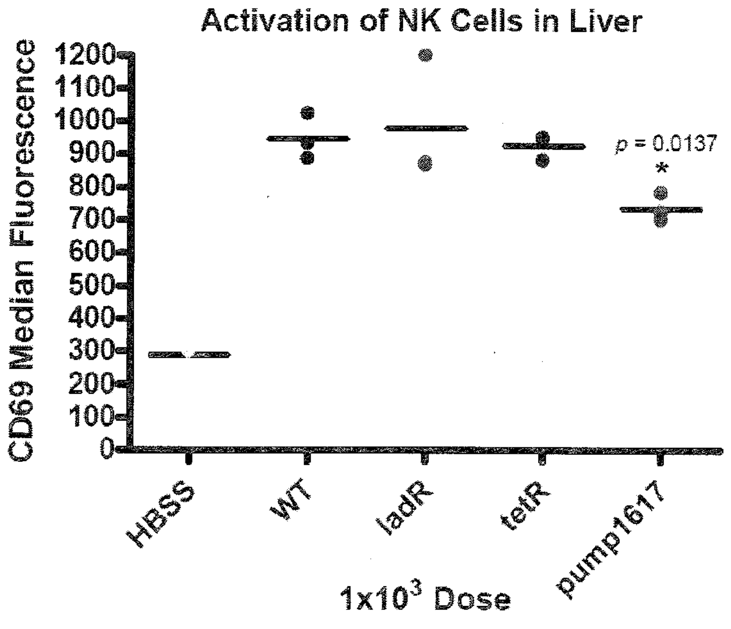
FIG. 17: includes a graph indicating that mdrM (pump1617) infection results in less NK activation than other mutant and w.t. *L. monocytogenes* strains.

To assess the effects of infection by ladR, tetR and mdrM (pump1617) mutant strains relative to w.t. with respect to NK cell maturation and activation, hepatocytes from Balb/c mice were harvested 2 days post-infection, as schematically shown in FIG. 15. Single cell suspensions were created, the cells were stained for known NK cell markers and flow cytometry performed on the labeled cells to assess NK maturation. FIG. 16 shows the results, which indicate that all strains, mutant and w.t., yielded similar liver NK cell maturation profiles. NK cell activation was then assessed by quantitating the number of CD11b+/DX5+ NK cells, as shown in FIG. 17. The results indicate that mdrM (pump1617) infection results in less NK activation than other mutants, which are comparable to w.t.

Figure 18:
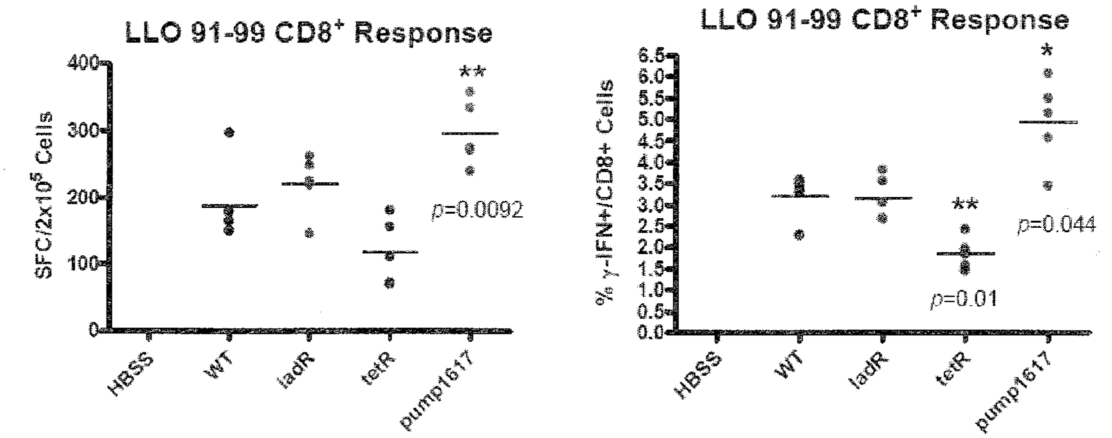
FIG. 18: includes a table and graphs showing experimental conditions and results indicating that MdrM (pump1617) infection induces a greater *L. monocytogenes* epitope-specific CD8+ T cell response than ladR and w.t. strains.
Figure 19:
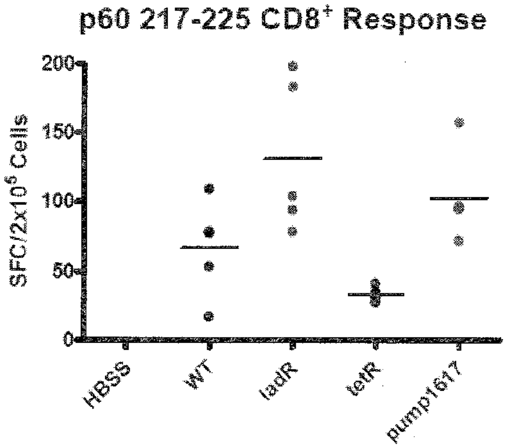
FIG. 19: includes a table and graphs showing experimental conditions and results indicating that tetR infection induces a reduced *L. monocytogenes* epitope-specific CD8+ T cell response relative to other mutant and w.t. strains.
Figure 19:
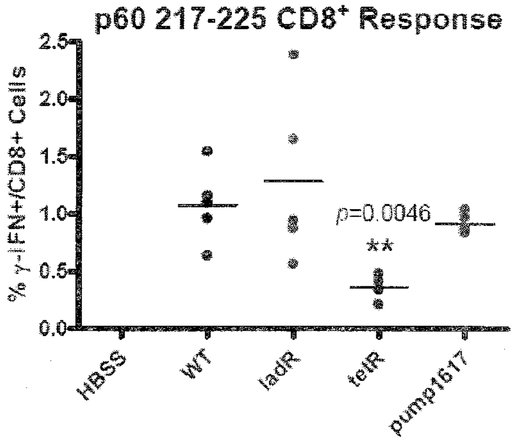
Figure 20:
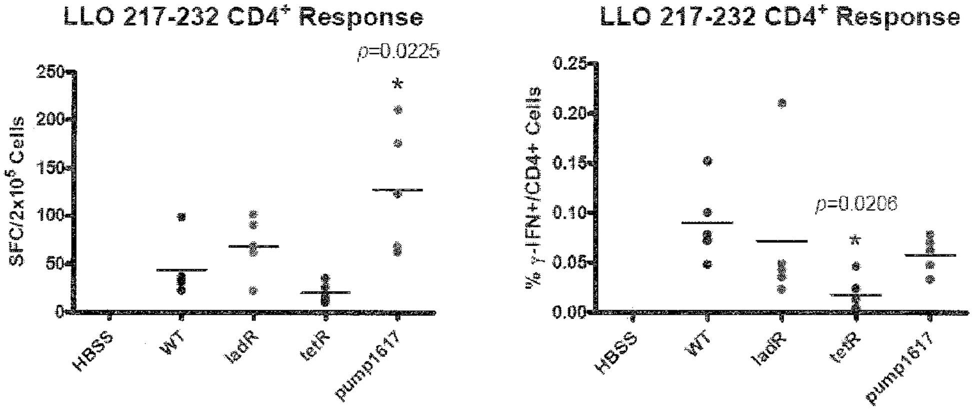
FIG. 20: includes a table and graphs showing experimental conditions and results indicating that CD4+ T cell specific epitopic response was reduced in the case of tetR and elevated relative to w.t. by mdrM (pump1617) infection.

Next, CD8+ T cell response to four *L. monocytogenes* epitopes was assessed, as shown in FIGS. 18 and 19. MdrM (pump1617) shows a greater *L. monocytogenes* epitope-specific CD8+ T cell response than ladR and w.t., which in turn is greater than that of tetR (FIG. 19). Similarly, CD4+ T cell specific epitopic response was reduced in the case of tetR and elevated relative to w.t. in the case of mdrM (pump1617). Accordingly, mutation of *L. monocytogenes* multidrug resistance transporter genes and their transcriptional regulators induces an altered Type I interferon response in the host.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. An attenuated *Listeria* bacterium comprising a mutation which modulates the expression of a multidrug resistance transporter, wherein said *Listeria* bacterium modulates interferon-β production in macrophages and when said mutation is a mutation in a transcription regulator gene, the mutation is a mutation in the TetR, LadR or MarR gene.

2. The *Listeria* bacterium according to claim 1, wherein said mutation is a mutation in a transcription regulator gene.

3. The *Listeria* bacterium according to claim 1, wherein said mutation is a mutation in a multidrug resistance transporter gene.

4. The *Listeria* bacterium according to claim 2, wherein said transcription regulator gene encodes a product that regulates a multidrug resistance transporter.

5. The *Listeria* bacterium according to claim 1, wherein said *Listeria* bacterium is *Listeria monocytogenes.*

6. The *Listeria* bacterium according to claim 1, wherein said bacterium comprises a heterologous nucleic acid.

7. The *Listeria* bacterium according to claim 6, wherein said heterologous nucleic acid encodes at least one product.

8. The *Listeria* bacterium according to claim 7, wherein said at least one product is an antigen.

9. A vaccine comprising an attenuated *Listeria* bacterium having a mutation which modulates the expression of a multidrug resistance transporter, wherein said attenuated *Listeria* bacterium modulates interferon-β production in macrophages and when said mutation is a mutation in a transcription regulator gene, the mutation is a mutation in the TetR, LadR or MarR gene.

10. The vaccine according to claim 9, wherein said mutation is a mutation in a transcription regulator gene.

11. The vaccine according to claim 9 wherein said mutation is a mutation in a multidrug resistance transporter gene.

12. The vaccine according to claim 11, wherein said multidrug resistance transporter gene is chosen from a MdrL gene, a MdrT gene and a MdrM gene.

13. The vaccine according to claim 9, wherein said mutation is chosen from an insertion mutation and a deletion mutation.

14. The *Listeria* bacterium according to claim 9, wherein said modulation of interferon-β production does not induce macrophage cell death.

15. The vaccine according to claim 9, wherein said *Listeria* bacterium is *Listeria monocytogenes*.

16. The vaccine according to claim 9, wherein said *Listeria* bacterium further comprises a mutation in a UvrA gene and/or a UvrB gene.

17. A method of eliciting or boosting a cellular immune response in a subject, said method comprising:

administering to said subject an effective amount of a vaccine comprising an attenuated *Listeria* bacterium having a mutation which modulates the expression of a multidrug resistance transporter, wherein said attenuated *Listeria* bacterium modulates interferon-β production in macrophages.

18. A *Listeria* bacterium comprising a mutation which modulates the expression of a multidrug resistance transporter, wherein said *Listeria* bacterium modulates interferon-β production in macrophages and expresses a heterologous antigen that provides protection in an animal against challenge by the infectious agent from which the heterologous antigen was derived or which modulates tumor growth and metastasis in a beneficial manner.

19. The *Listeria* bacterium according to claim 18, wherein said mutation is a mutation in a transcription regulator gene.

20. The *Listeria* bacterium according to claim 18, wherein said mutation is a mutation in a multidrug resistance transporter gene.

21. The *Listeria* bacterium according to claim 18, wherein said heterologous antigen comprises a fusion protein.

22. A *Listeria* bacterium comprising a mutation which modulates the expression of a multidrug resistance transporter, wherein said *Listeria* bacterium modulates interferon-β production in macrophages and comprises a mutation in a transcription regulator gene and a multidrug resistance transporter gene.

* * * * *

SEQUENCE LISTING

```
<160> NUMBER OF SEQ ID NOS: 13

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1

ctggagcagc tgaatggaaa g                                                21


<210> SEQ ID NO 2
<211> LENGTH: 21
<212> TYPE: DNA
<213> ORGANISM: Artificial Sequence
<220> FEATURE:
<223> OTHER INFORMATION: Synthetic Primer

<400> SEQUENCE: 2

cttgaagtcc gccctgtagg t                                                21
```

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
aggtgtgatg gtgggaatgg 20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
gcctcgtcac ccacatagga 20

<210> SEQ ID NO 5
<211> LENGTH: 19
<212> TYPE: DNA
<213> ORGANISM: Artificial Sequence
<220> FEATURE:
<223> OTHER INFORMATION: Synthetic Primer

<400> SEQUENCE: 5
caatagagag atgtcaccg 19

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer

<400> SEQUENCE: 6
gcggatgaag aggataatta cg 22

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
ggaatccata gatggaccgt ta 22

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
gggaaatgga taacagcggc 20

<210> SEQ ID NO 9
<211> LENGTH: 17
<212> TYPE: DNA
<213> ORGANISM: Artificial Sequence
<220> FEATURE:
<223> OTHER INFORMATION: Synthetic Primer -continued

<400> SEQUENCE: 9
gagcattgtc atcgcgg 17

<210> SEQ ID NO 10
<211> LENGTH: 25
<212> TYPE: DNA
<213> ORGANISM: Artificial Sequence
<220> FEATURE:
<223> OTHER INFORMATION: Synthetic Primer

<400> SEQUENCE: 10
ggtattttga ttgttatgct tatgg 25

<210> SEQ ID NO 11
<211> LENGTH: 25
<212> TYPE: DNA
<213> ORGANISM: Artificial Sequence
<220> FEATURE:
<223> OTHER INFORMATION: Synthetic Primer

<400> SEQUENCE: 11
ttgtaaatcg ttcaattaaa aaggc 25

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
aatagtacag cagtagaacg 20

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
ctgtaatatg caaatcatcc 20